United States Patent [19]
Anderson et al.

[11] Patent Number: 6,004,798
[45] Date of Patent: Dec. 21, 1999

[54] RETROVIRAL ENVELOPES HAVING MODIFIED HYPERVARIABLE POLYPROLINE REGIONS

[75] Inventors: W. French Anderson, San Marino; Bonnie Weimin Wu, Pasadena, both of Calif.

[73] Assignee: University of Southern California, Los Angeles, Calif.

[21] Appl. No.: 08/856,074

[22] Filed: May 14, 1997

[51] Int. Cl.$^6$ .............................. C12N 7/01; C12N 15/09; C12N 15/63; C12N 15/70
[52] U.S. Cl. .................................... 435/235.1; 435/320.1; 536/23.1
[58] Field of Search ............................. 435/235.1, 320.1; 536/23.1

[56] References Cited

U.S. PATENT DOCUMENTS

| | | | |
|---|---|---|---|
| 5,543,328 | 8/1996 | McClelland et al. | 435/320.1 |
| 5,591,624 | 1/1997 | Barber et al. | 435/240.2 |
| 5,643,756 | 7/1997 | Kayman et al. | 435/69.7 |
| 5,723,287 | 3/1998 | Russell et al. | 435/5 |

FOREIGN PATENT DOCUMENTS

| | | |
|---|---|---|
| WO92/06180 | 4/1992 | WIPO . |
| WO93/00103 | 1/1993 | WIPO . |
| WO93/09221 | 5/1993 | WIPO . |
| WO93/14188 | 7/1993 | WIPO . |
| WO93/20221 | 10/1993 | WIPO . |
| WO93/25234 | 12/1993 | WIPO . |
| WO94/06920 | 3/1994 | WIPO . |
| WO94/10323 | 5/1994 | WIPO . |
| WO94/11524 | 5/1994 | WIPO . |
| WO94/12626 | 6/1994 | WIPO . |
| WO94/27643 | 12/1994 | WIPO . |
| WO96/23882 | 8/1996 | WIPO . |
| WO96/30504 | 10/1996 | WIPO . |

OTHER PUBLICATIONS

Salmons, et al., *Human Gene Therapy*, vol. 4, pp. 129–141 (1993).
Barinaga, *Science*, vol. 266, p. 1326 (Nov. 25, 1994).
Kasahara, et al., *Science*, vol. 266, pp. 1373–1376 (Nov. 25, 1994).
Wong, et al., *Bone Marrow Transplantation Experimentation*, Abstract 1001 (Dec. 6, 1994).

*Primary Examiner*—Frank C. Eisenschenk
*Assistant Examiner*—Brett Nelson
*Attorney, Agent, or Firm*—Elliot M. Olstein; Raymond J. Lillie

[57] ABSTRACT

A retroviral vector particle having a modified retroviral envelope polypeptide. The retroviral envelope polypeptide includes the hypervariable polyproline region, or hinge region, and the hypervariable polyproline region, or hinge region is modified to include a targeting polypeptide including a binding region which binds to a ligand. Such a retroviral vector may be "targeted" to various cells for delivery of genetic material to such cells.

14 Claims, 6 Drawing Sheets

FIG. 1

Amphotropic PRO GPRVPIGPNPVLPDQRLPSSPIEIVPAPQPPSPLNTSYPPSTTSTPSTSPTSPSVPQPPP

Ecotropic PRO GPRVPIGPNPVLADQQPLSKPKPVKSPSVTKPPSGTPLSPTQLPP

FIG. 2

| SU | PRO | TM |

AvrII  NgoMI

| | Sequence | Neo$^R$ Titer |
|---|---|---|
| 5' 3' | GPRVPIGPNPVLPDQRLPSSPIEIVPAPQPPSPLNTSYPPSTTSTPSTSPSVPQPPP | $1.7 \times 10^6$ |
| C-14 | GPRVPIGPNPVLPDQRLPSSPIEIVPAPQPPSPLNTSYPPSTTSTP | $3.5 \times 10^6$ |
| C-19 | GPRVPIGPNPVLPDQRLPSSPIEIVPAPQPPSPLNTSYPPS | $3.2 \times 10^6$ |
| C-24 | GPRVPIGPNPVLPDQRLPSSPIEIVPAPQPPSPLNT | $2.8 \times 10^6$ |
| C-29 | GPRVPIGPNPVLPDQRLPSSPIEIVPAPQPP | $2.6 \times 10^6$ |
| C-34 | GPRVPIGPNPVLPDQRLPSSPIEIVP | $1.0 \times 10^6$ |
| C-39 | GPRVPIGPNPVLPDQRLPSSP | $1.1 \times 10^5$ |
| C-44 | GPRVPIGPNPVLPDQR | $1.8 \times 10^5$ |
| C-49 | GPRVPIGPNPV | $2.0 \times 10^5$ |
| C-54 | GPRVPI | 0 |
| N-14 | QRLPSSPIEIVPAPQPPSPLNTSYPPSTTSTPSTSPSVPQPPP | 0 |
| WT CEE+ | | $4.0 \times 10^6$ |

CEE+ 5'-3' N-del C-del gp85
gp70

CEE+5'-3' N-del C-del

—SU
—CA
—TM

—SU
—CA

—TM

CEE+

N-14

RETROVIRAL ENVELOPES HAVING MODIFIED HYPERVARIABLE POLYPROLINE REGIONS

This invention relates to a polypeptide which is a modified viral envelope. This invention further relates to "targeted" retroviral vector particles. More particularly, this invention relates to retroviral vector particles having a modified, or chimeric, envelope polypeptide, wherein the hypervariable polyproline region, also known as the hinge region, of the envelope polypeptide is modified to include a targeting polypeptide including a binding region which binds to a ligand. The term "polypeptide" as used herein means a polymer of amino acids and does not refer to any particular length of polymer. Such term also includes post-translationally modified polypeptides or proteins (e.g., glycosylated, acetylated, phosphorylated, etc.). The term "ligand", as used herein, means a molecule which is capable of being bound by the targeting polypeptide. Such molecules include, but are not limited to, cellular receptors and extracellular components such as extracellular matrix components.

BACKGROUND OF THE INVENTION

Retroviral vector particles are useful agents for introducing polynucleotides into cells, such as eukaryotic cells. The term "introducing" as used herein encompasses a variety of methods of transferring polynucleotides into a cell, such methods including transformation, transduction, transfection, and transinfection.

Retroviruses typically have three common open reading frames, gag, pol, and env, which encode the structural proteins, encode enzymes including reverse transcriptase, and encode an envelope protein, respectively. Typically, retroviral vector particles are produced by packaging cell lines that provide the necessary gag, pol, and env gene products in trans. (Miller, et al., *Human Gene Therapy*, Vol. 1, pgs. 5–14 (1990)). This approach results in the production of retroviral vector particles which transduce mammalian cells, but are incapable of further replication after they have integrated into the genome of the cell.

Thus, retroviral vector particles have been used for introducing polynucleotides into cells for gene therapy purposes. In one approach, cells are obtained from a patient, and retroviral vector particles are used to introduce a desired polynucleotide into the cells, and such modified cells are returned to the patient for a therapeutic purpose. See Anderson et al., U.S. Pat. No. 5,399,346, issued Mar. 21, 1995. In another approach, retroviral vector particles may be administered to the patient in vivo, whereby the retroviral vector particles transduce cells of the patient in vivo.

In many gene therapy protocols, it would be desirable to target retroviral vector particle infection to a specific population of cells either in vivo or in vitro. In such circumstances, the broad host range of typical retroviruses presents a significant problem. A key determinant of viral host range is the "envelope" or "env" protein (encoded by the env gene) which is involved in binding to receptors on the surface of susceptible cells. Where it is possible to purify the desired target cells, either before or after transduction, such purification necessitates undesirable manipulations of the cells and may be problematic in situations in which the preferred target cells either are difficult to purify or are present at low or variable frequencies in mixed cell populations. Thus, it would be advantageous to have retroviral vector particles which could infect particular types of mammalian cells.

Generation of a targeting retroviral vector particle would enable the recombinant retrovirus to deliver a therapeutic gene to the target tissue through cross-species and/or tissue-specific infection. To achieve such a goal, common strategies have been to modify the natural host range determinant, the retroviral envelope protein, by inserting new receptor binding polypeptides into the surface domain (SU) of the envelope protein. The envelope protein, however, is difficult to modify. Prior attempts to modify the retroviral envelope have been directed to the insertion of targeting polypeptides into the receptor binding region of the envelope protein. Such attempts have resulted in the disruption of the envelope structure to such an extent that the folding, processing, and incorporation of the envelope protein is impaired strongly. Also, the activity of the inserted polypeptide may be limited by the steric hindrance caused by the surrounding host protein residues.

SUMMARY OF THE INVENTION

The present invention is directed to retroviruses having modified envelopes. More specifically, the polyproline hypervariable region of the retroviral envelope protein is modified such that the hypervariable polyproline region includes a targeting polypeptide which binds to a ligand. The ligand may be a receptor located on a desired type of cell or may be an extracellular matrix component, such as collagen, for example. Such "targeted" retroviral vectors enable one to deliver desired genes to a variety of cell types.

Applicants have found that the hypervariable polyproline region of the surface domain, which is located next to the receptor binding region, is independent and flexible. The hypervariable polyproline region can be as short as the 11 amino acid residues at the N-terminal and still provide a viral titer of up to $2 \times 10^5$ cfu/ml. The hypervariable polyproline region also can be made longer than the wild type (i.e., unmodified) hypervariable polyproline region. As shown in Example 6, below, when a collagen binding domain is inserted into the hypervariable polyproline region, the virus which is pseudotyped with such a chimeric envelope can bind to a collagen-coated plate. This indicates that polypeptides inserted into the hypervariable polyproline region can be exposed to the envelope protein surface, and the virus can bind to an extracellular matrix component or a molecule located on the surface of a target cell. Furthermore, the hypervariable polyproline region can be an extended region, which largely eliminates the steric hindrance toward the inserted polypeptide domain caused by the surrounding host protein residues. Thus, applicants have found that one can generate an efficient recombinant retroviral vector particle by inserting a targeting polypeptide into the hypervariable polyproline region of a retroviral envelope protein.

BRIEF DESCRIPTION OF THE DRAWINGS

The invention now will be described with respect to the drawings, wherein:

FIG. 1 is a schematic display of the sequence alignment between the amphotropic and ecotropic proline-rich hypervariable polyproline regions. The upper line shows the sequence of the entire amphotropic hypervariable polyproline region, while the lower line shows the ecotropic hypervariable polyproline sequence. The N-terminal conserved 14 amino acids are underlined.

FIG. 2 shows a representation of serial truncations from the C-terminal end of the amphotropic hypervariable polyproline and the corresponding titers. The "PRO" displayed on the top of the figure represents the proline-rich region in the ecotropic envelope protein. AvrII and NgoMI flanking the PRO region are the two enzymes utilized to swap the different lengths of the amphotropic hypervariable polyproline sequence. The amino acid sequences are the truncated amphotropic hypervariable polyproline sequences cloned into the corresponding region of the ecotropic envelope protein. 5'-3' indicates the construct in which the entire amphotropic hypervariable polyproline is inserted. The constructs containing the deletions from the C-terminal end of the amphotropic hypervariable polyproline are named based on the number of amino acids deleted. For example, the number in C-14 indicates that 14 amino acids are truncated from the C-terminal end of the amphotropic hypervariable polyproline. N-14 represents the mutant in which the N-terminal 14 conserved amino acids are deleted. CEE+ stands for the wild type ecotropic envelope protein. The numbers on the right side of the figure shows the neo$^R$ titer corresponding to each envelope construct.

FIG. 3A Envelope proteins in the producer cell lysates. The upper band represents the unprocessed surface precursor (gp85). The lower band shows the mature surface protein (gp70).

Figure 3A:
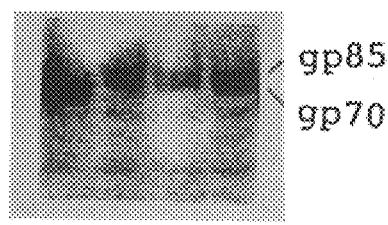
FIGS. 3A and B show detection of envelope protein in producer cell lysates and in viral particles.

Other targeting peptides which may be employed include cytokines. Such cytokines include, but are not limited to, interleukins, including Interleukin-1α, Interleukin-1β, and Interleukins 2 through 14; growth factors such as epithelial growth factor (EGF), TGF-α, TGF-β, fibroblast growth factor (FGF), keratinocyte growth factor (KGF), PDGF-A, PDGF-B, PD-ECGF, IGF-I, IGF-II, and nerve growth factor (NGF), which binds to the NGF receptor of neural cells; colony stimulating factors such as GM-CSF, G-CSF, and M-CSF, leukemic inhibitory factor (LIF); interferons such as interferon-α, interferon-β, and interferon-γ; inhibin A; inhibin B; chemotactic factors; α-type intercrine cytokines; and β-type intercrine cytokines.

Still other targeting polypeptides which may be employed include, but are not limited to, melanoma stimulating hormone, which binds to the MSH receptor on melanoma cells; the polypeptide FLA16, which has the sequence Cys-Gln-Ala-Gly-Thr-Phe-Ala-Leu-Arg-Gly-Asp-Asn-Pro-Gln-Gly-Cys (SEQ ID NO:40), which binds to the integrins VLA3, VLA4, and VLA5 found on human histiocytic lymphoma cells; the polypeptide having the structure Gly-Glu-Arg-Gly-Asp-Gly-Ser-Phe-Phe-Ala-Phe-Arg-Ser-Pro-Phe (SEQ ID NO:41), which binds to the integrin $\alpha v\beta_3$ found on melanoma cells; erythropoietin, which binds to the erythropoietin receptor; adherins; selecting; CD34, which binds to the CD34 receptor of hematopoietic stem cells; CD33, which binds to premyeloblastic leukemia cells; stem cell factor; asialoglycoproteins, including asialoorosomucoid, asialofetuin, and alpha-1 acid glycoprotein, which binds to the asialoglycoprotein receptor of liver cells; insulin; glucagon; gastrin polypeptides, which bind to receptors on hematopoietic stem cells; C-kit ligand; tumor necrosis factors (Qr TNF's) such as, for example, TNF-alpha and TNF-beta; ApoB, which binds to the LDL receptor of liver cells; alpha-2-macroglobulin, which binds to the LRP receptor of liver cells; mannose-containing peptides, which bind to the mannose receptor of macrophages; sialyl-Lewis-X antigen-containing peptides, which bind to the ELAM-1 receptor of activated endothelial cells; CD40 ligand, which binds to the CD40 receptor of B-lymphocytes; ICAM-1, which binds to the LFA-1 (CD11b/CD18) receptor of lymphocytes, or to the Mac-1 (CD11a/CD18) receptor of macrophages; M-CSF, which binds to the c-fms receptor of spleen and bone marrow macrophages; VLA-4, which binds to the VCAM-1 receptor of activated endothelial cells; LFA-1, which binds to the ICAM-1 receptor of activated endothelial cells; HIV gp120 and Class II MHC antigen, which bind to the CD4 receptor of T-helper cells; and the LDL receptor binding region of the apolipoprotein E (ApoE) molecule. It is to be understood, however, that the scope of the present invention is not to be limited to any specific targeting polypeptide.

In one embodiment, the targeting polypeptide is a single chain antibody.

In another embodiment, the targeting polypeptide includes a binding region which binds to an extracellular matrix component. The term "extracellular matrix component," as used herein, means a molecule that occupies the extracellular spaces of tissues. Such extracellular matrix components include, but are not limited to, collagen (including collagen Type I and collagen Type IV), laminin, fibronectin, elastin, glycosaminoglycans, proteoglycans, and sequences which bind to fibronectin, such as arginine-glycine-aspartic acid, or RGD, sequences. Binding regions which bind to an extracellular matrix component, and which may be included in a targeting polypeptide, include, but are not limited to, polypeptide domains which are functional domains within von Willebrand Factor or derivatives thereof, wherein such polypeptide domains bind to collagen. In one embodiment, the binding region is a polypeptide having the amino acid sequence of residues 4 through 13 of SEQ ID NO:19.

Other binding regions which bind to an extracellular matrix component, and which may be included in the viral envelope, include, but are not limited to, the arginine-glycine-aspartic acid, or RGD, sequences, which binds fibronectin, and a polypeptide having the sequence Gly-Gly-Trp-Ser-His-Trp, which also binds to fibronectin.

In addition to the binding region, the targeting polypeptide may further include linker sequences of one or more amino acid residues, placed at the N-terminal and/or C-terminal of the binding region, whereby such linkers increase rotational flexibility and/or minimize stearic hindrance of the modified envelope polypeptide.

It is to be understood, however, that the scope of the present invention is not to be limited to any specific targeting polypeptide, binding region, or ligand to which the targeting polypeptide may bind.

In accordance with another aspect of the present invention, there is provided a modified polynucleotide encoding a modified retroviral envelope polypeptide for targeting a retroviral vector particle to a ligand. The retroviral envelope polypeptide includes the hypervariable polyproline region. In the modified polynucleotide, the polynucleotide encoding the hypervariable polyproline region is modified to include a polynucleotide encoding a targeting polypeptide including a binding region which binds to a ligand.

In one embodiment, prior to modification, the polynucleotide encoding the hypervariable polyproline region encodes the sequence of (SEQ ID NO:1). In the modified polynucleotide, a polynucleotide including the codons encoding amino acid residues 34 through 49 are removed and replaced with the polynucleotide encoding the targeting polypeptide. In another embodiment, in the modified polynucleotide, the polynucleotide encoding the targeting polypeptide is inserted between the codon encoding amino acid residue 35 and the codon encoding amino acid residue 36 of (SEQ ID NO:1). The hypervariable polyproline region having the sequence (SEQ ID NO:1) is encoded by the polynucleotide having (SEQ ID NO:2) or a degenerative derivative or analogue thereof.

The term “derivative or analogue thereof” as used herein means that the polynucleotide encoding the polypeptide (SEQ ID NO:1) may have a sequence different from the polynucleotide (SEQ ID NO:2), yet encode the same polypeptide. Such differences in polynucleotide sequences may, for example, be due to the degeneracy of the genetic code. It is also contemplated within the scope of the present invention that, prior to the modification of (SEQ ID NO:2) with a polynucleotide encoding a targeting polypeptide, (SEQ ID NO:2) may be modified such that one or more codons are changed such that the codons modify different amino acid residues than the unmodified sequences. Such modifications may facilitate the insertion of the polynucleotide encoding the targeting polypeptide. For example, (SEQ ID NO:2) may be modified such that the codon encoding amino acid residue 35 of (SEQ ID NO:1) may be changed such that the codon encodes glutamine instead of asparagine, the codon encoding amino acid residue 48 of (SEQ ID NO:1) may be changed such that the codon encodes glycine instead of threonine, and the codon encoding amino acid residue 49 of (SEQ ID NO:1) may be changed such that the codon encodes leucine instead of serine.

The above polynucleotides may be constructed by genetic engineering techniques known to those skilled in the art. For example, a first expression plasmid may be constructed which includes a polynucleotide encoding the unmodified envelope. The plasmid then is engineered such that a polynucleotide encoding the targeting polypeptide is inserted between two codons encoding consecutively numbered amino acid residues of the unmodified envelope, or is engineered such that a polynucleotide encoding a portion of the unmodified envelope is removed, whereby such portion may be replaced with a polynucleotide encoding the targeting polypeptide. The polynucleotide encoding the targeting polypeptide may be contained in a second expression plasmid or may exist as a naked polynucleotide sequence. The polynucleotide encoding the targeting polypeptide or the plasmid containing such polynucleotide is cut at appropriate restriction enzyme sites and cloned into the first expression plasmid which also has been cut at appropriate restriction enzyme sites. The resulting expression plasmid thus includes a polynucleotide encoding the modified envelope protein. Such polynucleotide then may be cloned out of the expression plasmid, and into a retroviral plasmid vector.

The term “polynucleotide” as used herein means a polymeric form of nucleotide of any length, and includes ribonucleotides and deoxyribonucleotides. Such term also includes single- and double-stranded DNA, as well as single- and double-stranded RNA. The term also includes modified polynucleotides such as methylated or capped polynucleotides.

In a preferred embodiment, the viral vector particle having a modified envelope in accordance with the invention includes a polynucleotide encoding a heterologous polypeptide which is to be expressed in a desired cell. The heterologous polypeptide may, in one embodiment, be a therapeutic agent. The term “therapeutic” is used in a generic sense and includes treating agents, prophylactic agents, and replacement agents.

Polynucleotides encoding therapeutic agents which may be contained in the retroviral vector particle include, but are not limited to, polynucleotides encoding tumor necrosis factor (TNF) genes, such as TNF-α; genes encoding interferons such as Interferon-α, Interferon-β, and Interferon-γ; genes encoding interleukins such as IL-1, IL-1β, and Interleukins 2 through 14; anticoagulants; anti-platelet agents; anti-inflammatory agents; the erythropoietin gene; genes encoding G-CSF, GM-CSF, TGF-α, TGF-β, and fibroblast growth factor; genes encoding adenosine deaminase, or ADA; genes which encode cellular growth factors, such as lymphokines, which are growth factors for lymphocytes; genes encoding epidermal growth factor (EGF), vascular endothelial growth factor (VEGF), and keratinocyte growth factor (KGF); genes encoding soluble CD4; gene encoding clotting factors, including Factor VIII, Factor IX, protein S, protein C, antithrombin III, and von Willebrand Factor; cytochrome b; glucocerebrosidase; T-cell receptors; the LDL receptor, ApoE, ApoC, ApoAI and other genes involved in cholesterol transport and metabolism; the alpha-1 antitrypsin (α1AT) gene; the insulin gene; the hypoxanthine phosphoribosyl transferase gene; the cystic fibrosis transmembrane conductance regulator (CFTR) gene; negative selective markers or “suicide” genes, such as viral thymidine kinase genes, such as the Herpes Simplex Virus thymidine kinase gene, the cytomegalovirus virus thymidine kinase gene, and the varicella-zoster virus thymidine kinase gene; Fc receptors for antigen-binding domains of antibodies, antisense sequences which inhibit viral replication, such as antisense sequences which inhibit replication of hepatitis B or hepatitis non-A non-B virus; antisense c-myb oligonucleotides; and antioxidants such as, but not limited to, manganese superoxide dismutase (Mn-SOD), catalase, copper-zinc-superoxide dismutase (CuZn-SOD), extracellular superoxide dismutase (EC-SOD), and glutathione reductase; tissue plasminogen activator (tPA); urinary plasminogen activator (urokinase); hirudin; the phenylalanine hydroxylase gene; nitric oxide synthetase; vasoactive peptides; angiogenic peptides; the dopamine gene; the dystrophin gene; the β-globin gene; the α-globin gene; the HbA gene; protooncogenes such as the ras, src, and bcl genes; tumor-suppressor genes such as p53 and Rb; the LDL receptor; the heregulin-α protein gene, for treating breast, ovarian, gastric and endometrial cancers; polynucleotides encoding cell cycle control agents, agents which inhibit cyclin proteins, such as antisense polynucleotides to the cyclin G1 and cyclin D1 genes; monoclonal antibodies specific to epitopes contained within the β-chain of a T-cell antigen receptor; the multidrug resistance (MDR) gene; polynucleotides encoding ribozymes; antisense polynucleotides; genes encoding secretory peptides which act as competitive inhibitors of angiotensin converting enzyme, of vascular smooth muscle calcium channels, or of adrenergic receptors, and polynucleotides encoding enzymes which break down amyloid plaques within the central nervous system. It is to be understood, however, that the scope of the present invention is not to be limited to any particular therapeutic agent.

The polynucleotide encoding the therapeutic agent is under the control of a suitable promoter. Suitable promoters which may be employed include, but are not limited to, the retroviral LTR; the SV40 promoter; the cytomegalovirus (CMV) promoter; the Rous Sarcoma Virus (RSV) promoter; the histone promoter; the polIII promoter, the β-actin promoter; inducible promoters, such as the MMTV promoter, the metallothionein promoter; heat shock promoters; adenovirus promoters; the albumin promoter; the ApoAI promoter; B19 parvovirus promoters; human globin promoters; viral thymidine kinase promoters, such as the Herpes Simplex thymidine kinase promoter; retroviral LTRs; human growth hormone promoters, and the MxIFN inducible promoter. The promoter also may be the native promoter which controls the polynucleotide encoding the therapeutic agent. It is to be understood, however, that the scope of the present invention is not to be limited to specific foreign genes or promoters.

The polynucleotides encoding the modified envelope polypeptide and the therapeutic agent may be placed into an appropriate retroviral plasmid vector by genetic engineering techniques known to those skilled in the art.

In one embodiment, the retroviral plasmid vector may be derived from Moloney Murine Leukemia Virus and is of the LN series of vectors, such as those hereinabove mentioned, and described further in Bender, et al., *J. Virol.*, Vol. 61, pgs. 1639–1649 (1987) and Miller, et al., *Biotechniques*, Vol. 7, pgs 980–990 (1989). Such vectors have a portion of the packaging signal derived from a mouse sarcoma virus, and a mutated gag initiation codon. The term "mutated" as used herein means that the gag initiation codon has been deleted or altered such that the gag protein or fragments or truncations thereof, are not expressed.

In another embodiment, the retroviral plasmid vector may include at least four cloning, or restriction enzyme recognition sites, wherein at least two of the sites have an average frequency of appearance in eukaryotic genes of less than once in 10,000 base pairs; i.e., the restriction product has an average DNA size of at least 10,000 base pairs. Preferred cloning sites are selected from the group consisting of NotI, SnaBI, SalI, and XhoI. In a preferred embodiment, the retroviral plasmid vector includes each of these cloning sites. Such vectors are further described in U.S. Pat. No. 5,672,510, and incorporated herein by reference in their entirety.

When a retroviral plasmid vector including such cloning sites is employed, there may also be provided a shuttle cloning vector which includes at least two cloning sites which are compatible with at least two cloning sites selected from the group consisting of NotI, SnaBI, SalI, and XhoI located on the retroviral plasmid vector. The shuttle cloning vector also includes at least one desired polynucleotide encoding a therapeutic agent which is capable of being transferred from the shuttle cloning vector to the retroviral plasmid vector.

The shuttle cloning vector may be constructed from a basic "backbone" vector or fragment to which are ligated one or more linkers which include cloning or restriction enzyme recognition sites. Included in the cloning sites are the compatible, or complementary cloning sites hereinabove described. Genes and/or promoters having ends corresponding to the restriction sites of the shuttle vector may be ligated into the shuttle vector through techniques known in the art.

The shuttle cloning vector can be employed to amplify DNA sequences in prokaryotic systems. The shuttle cloning vector may be prepared from plasmids generally used in prokaryotic systems and in particular in bacteria. Thus, for example, the shuttle cloning vector may be derived from plasmids such as pBR322; pUC 18; etc.

The retroviral plasmid vector includes one or more promoters for the genes contained in the vector. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, TK promoters, and B19 parvovirus promoters. The selection of a suitable promoter will be apparent to those skilled in the art from the teachings contained herein.

In one embodiment, the retroviral plasmid vector, which includes a polynucleotide encoding the modified envelope protein and a polynucleotide encoding a heterologous protein or polypeptide therapeutic agent, is employed to transduce a packaging cell line to form a producer cell line, which will generate infectious retroviral vector particles. Alternatively, a naked polynucleotide sequence encoding the modified envelope protein is transfected into a "pre-packaging" cell line including nucleic acid sequences encoding the gag and pol proteins, thereby forming a packaging cell line, or is transfected into a packaging cell line including nucleic acid sequences encoding the gag, pol, and wild-type (i.e., unmodified) env proteins, thereby forming a packaging cell line including nucleic acid sequences encoding wild-type env protein and the modified envelope protein. Examples of such "pre-packaging" cell lines include, but are not limited to, GP8 cells, GPL cells, and GPNZ cells as described in Morgan, et al., *J. Virol.*, Vol. 67, No. 8, pgs. 4712–4721 (August 1993). Such cell lines, upon transduction with the retroviral plasmid vector, generates infectious retroviral particles including the modified, or chimeric, envelope and a polynucleotide encoding the therapeutic agent.

In another embodiment, a retroviral plasmid vector which includes a polynucleotide encoding a modified polynucleotide encoding a modified envelope polypeptide in accordance with the invention and a polynucleotide encoding a therapeutic agent is used to transduce a packaging cell line including nucleic acid sequences encoding the gag, pol, and wild-type (i.e., unmodified) env retroviral proteins. Examples of such packaging cell lines include, but are not limited to, the PE501, PA317 (ATCC No. CR19078), ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, and use of liposomes, such as hereinabove described, and $CaPO_4$ precipitation. Such producer cells generate infectious retroviral vector particles which include the modified envelope, the wild-type retroviral envelope, a polynucleotide encoding the modified, or chimeric, envelope, and a polynucleotide encoding a therapeutic agent.

In another embodiment, there is provided a packaging cell which includes a nucleic acid sequence encoding a modified chimeric envelope in accordance with the invention, and which may further include nucleic acid sequences encoding the gag and pol proteins. A producer cell for generating viral particles which includes a modified envelope in accordance with the invention is produced by introducing into such packaging cell either a retroviral vector particle or a retroviral plasmid vector, in each case including a polynucleotide encoding a therapeutic agent. The producer cell line thus generates infectious retroviral particles including the modified chimeric envelope and the polynucleotide encoding the therapeutic agent.

The retroviral vector particles, which include the modified envelope, and a polynucleotide encoding a therapeutic agent, may be administered to a host in an amount effective to produce a therapeutic effect in the host. The host may be a mammalian host, which may be a human or non-human primate host. The retroviral vector particles, upon administration to the host, travel to and transduce the desired target cells, whereby the transduced target cells express the therapeutic agent in vivo. The exact dosage of retroviral vector particles which may be administered is dependent upon a variety of factors, including the age, sex, and weight of the patient, the target cells which are to be transduced, the therapeutic agent which is to be administered, and the severity of the disorder to be treated.

The retroviral vector particles may be administered systemically, such as, for example, by intravenous, intraperitoneal, intracolonic, intratracheal, endotracheal, intranasal, intravascular, intrathecal, intraarterial, intracranial, intramarrow, intravesicular, intrapleural, intradermal, subcutaneous, intramuscular, intraocular, intraosseous, and intrasynovial administration. The retroviral vector particles also may be administrated topically.

Cells which may be transduced with the retroviral vector particles of the present invention include, but are not limited to, primary cells, such as primary nucleated blood cells, primary tumor cells, endothelial cells, epithelial cells, vascular cells, keratinocytes, stem cells, hepatocytes, chrondocytes, connective tissue cells, fibroblasts and fibroelastic cells of connective tissues, mesenchymal cells, mesothelial cells, and parenchymal cells; smooth muscle cells of the vasculature; hematopoietic stem cells; T-lymphocytes; B-lymphocytes; neutrophils; macrophages; platelets; erythrocytes; reparative mononuclear granulocytic infiltrates of inflamed tissues; nerve cells; brain cells; muscle cells; osteocytes and osteoblasts in bone; lung cells, pancreatic cells; epithelial and subepithelial cells of the gastrointestinal and respiratory tracts; and malignant and non-malignant tumor cells. The selection of the particular cells which are to be transduced is dependent upon the disease or disorder to be treated as well as the targeting polypeptide contained in the modified envelope. It is to be understood that the scope of the present invention is not to be limited to the transduction of any specific target cells.

Diseases or disorders which may be treated with the retroviral vector particles of the present invention include, but are not limited to, severe combined immune deficiency caused by adenosine deaminase deficiency; sickle cell anemia; thalassemia; hemophilia A and B; diabetes; emphysema caused by α-1-antitrypsin deficiency; Alzheimer's disease; AIDS; chronic granulomatosis; Gaucher's disease; Lesch-Nyhan syndrome; muscular dystrophy, including Duchenne muscular dystrophy; Parkinson's disease; cystic fibrosis; phenylketonuria; hypercholesterolemia; and other illnesses such as growth disorders and heart diseases, such as, for example, those caused by alterations in the way cholesterol is metabolized and defects in the immune system.

The retroviral vector particles also may be employed in the treatment of tumors, including malignant and non-malignant tumors. For example, a retroviral vector particle including a modified envelope protein, including a targeting polypeptide which binds to a tumor cell, and a polynucleotide encoding a negative selective marker or "suicide" gene, such as, for example, the Herpes Simplex Virus thymidine kinase (TK) gene, may be administered to a patient, whereby the retroviral vector particles transduce the tumor cells. After the tumor cells are transduced with the retroviral vector particles, an interaction agent or prodrug, such as gancyclovir or acyclovir, is administered to the patient, whereby the transduced tumor cells are killed.

When the retroviral vector particles include a targeting polypeptide which binds to an extracellular matrix component, such retroviral vector particles may be employed in treating diseases or disorders which are associated with an exposed extracellular matrix component. Such diseases or disorders include, but are not limited to, cardiovascular diseases; cirrhosis of the liver; and connective tissue disorders (including those associated with ligaments, tendons, and cartilage), and vascular disorders associated with the exposition of collagen. The retroviral vector particles may be used to deliver therapeutic genes to restore endothelial cell function and to combat thrombosis, in addition to limiting the proliferative and fibrotic responses associated with neointima formation. The retroviral vector particles also may be employed in treating vascular lesions; ulcerative lesions; areas of inflammation; sites of laser injury, such as the eye, for example; sites of surgery; arthritic joints; scars; and keloids. The retroviral vector particles also may be employed in wound healing.

In addition, retroviral vector particles which include a targeting polypeptide which binds to an extracellular matrix component in the hypervariable polyproline region also may be employed in the treatment of tumors, including malignant and non-malignant tumors. Although Applicants do not intend to be limited to any theoretical reasoning, tumors, when invading normal tissues or organs, secrete enzymes such as collagenases or metalloproteinases which provide for the exposition of extracellular matrix components. By targeting retroviral vector particles to such exposed extracellular matrix components, the retroviral vector particles become concentrated at the exposed matrix components which are adjacent the tumor, whereby the retroviral vector particles then infect the tumor cells. Such tumors include, but are not limited to, carcinomas; sarcomas, including chondrosarcoma, osteosarcoma, and fibrosarcoma; and brain tumors. For example, a retroviral vector particle, including a modified hypervariable polyproline region of the envelope protein, including a targeting polypeptide which binds to an extracellular matrix component located at a tumor site, and a polynucleotide encoding a negative selective marker or "suicide" gene, such as, for example, the Herpes Simplex Virus thymidine kinase (TK) gene, may be administered to a patient, whereby the retroviral vector particles transduce the tumor cells. After the tumor cells are transduced with the retroviral vector particles, an interaction agent or prodrug, such as gancyclovir or acyclovir, is administered to the patient, whereby the transduced tumor cells are killed.

Other polynucleotides encoding anti-tumor agents which may be contained in the retroviral vector particles include, but are not limited to, polynucleotides encoding cell cycle control agents, polynucleotides (such as, for example, antisense polynucleotides) which bind to polynucleotides encoding cyclin G1 or cyclin D1, tumor suppressor proteins, anti-angiogenic factors, such as, for example, endothelial monocyte activating polypeptide-2 (EMAP-2), cytokines and growth factors, which include those cytokines and growth factors hereinabove described. Growth of the tumor cells is inhibited, suppressed, or destroyed upon expression of the anti-tumor agent by the transduced tumor cells.

It is to be understood that the present invention is not to be limited to the treatment of any particular disease or disorder.

The retroviral vector particles, which include the modified envelope protein and a polynucleotide encoding a therapeutic agent, may be administered to an animal in vivo as part of an animal model for the study of the effectiveness of a gene therapy treatment. The retroviral vector particles may be administered in varying doses to different animals of the same species, whereby the retroviral vector particles will transduce the desired target cells in the animal. The animals then are evaluated for the expression of the desired therapeutic agent in vivo in the animal. From the data obtained from such evaluations, one may determine the amount of retroviral vector particles to be administered to a human patient.

The retroviral vector particles of the present invention also may be employed in the in vitro transduction of desired target cells, which are contained in a cell culture containing a mixture of cells. Upon transduction of the target cells in vitro, the target cells produce the therapeutic agent or protein in vitro. The therapeutic agent or protein then may be obtained from the cell culture by means known to those skilled in the art.

The retroviral vector particles also may be employed for the transduction of cells in vitro in order to study the mechanism of the genetic engineering of cells in vitro.

In addition, the modified envelope polypeptides of the present invention may be employed to form proteoliposomes; i.e., the modified envelope polypeptide forms a portion of the liposome wall. Such proteoliposomes may be employed for gene transfer or for drug delivery to desired target cells.

The invention now will be described with respect to the following examples; however, the scope of the present invention is not intended to be limited thereby.

EXAMPLE 1

Effects of swapping different lengths of the amphotropic hypervariable polyproline sequence into the corresponding region of the ecotropic envelope protein The structures of the amphotropic and ecotropic hypervariable polyproline regions are shown schematically in FIG. 1.

To test the flexibility of the hypervariable polyproline region, various lengths of the proline-rich sequence derived from the amphotropic hypervariable polyproline were inserted into the corresponding region of the ecotropic envelope protein (FIG. 2). One insert contained the entire 60 amino acid amphotropic hypervariable polyproline that is 15 amino acids longer than the ecotropic hypervariable polyproline. The resulting chimeric envelope was named 5'-3'. Two other inserts were amphotropic hypervariable polyprolines with a 14 amino acid deletion at either the N-terminus or the C-terminus, respectively, generating the same length hypervariable polyproline as that of the ecotropic envelope protein. Chimeric envelopes with these two inserts were named N-14 and C-14, as shown in FIG. 2. Such inserts were made by modifying the envelope expression vector Cee+, which is a CMV-env expression vector constructed by digesting Cee (Morgan, et. al., J. Virol, Vol. 67, No. 8, pgs. 4712–4721 (August 1993)) with HindIII and NotI, filling in the NotI site with a Klenow fragment, and ligating the CMV-env cassette into pBluescriptII SK+ (Stratagene, La Jolla, Calif.) digested with SmaI and HindIII.

In order to insert the amphotropic hypervariable polyproline regions into Cee+, AvrII and NgoMI sites were generated in Cee+ which flanked the 5' and 3' ends, respectively, of the ecotropic hypervariable polyproline.

To generate the envelope expression plasmids 5'-3', C-14, C-19, C-24, C-29, C-34, C-39, the corresponding amphotropic hypervariable polyproline regions were amplified by PCR amplification. The PCR reactions have a common sense primer. Each deletion has its own antisense primer. The primer sequences are presented below:

```
Sense primer:     5'-GACCTCCTAGGACCCCGAGTCCCCATAGGGCCCA-3'   (SEQ ID NO:3)

Anitsense primer:

5'-3'        5'-CGGTAGCCGGCTGGGGGTGGCTGTGGGACACTTGGAC-3'(SEQ ID NO:4)

C-14         5'-CGGTAGCCGGCGGGTGTACTGGTAGTGGAGGGGGG-3'  (SEQ ID NO:5)

C-19         5'-CGGTAGCCGGCGGAAGGGGGGTAACTGGTATTGAGG-3' (SEQ ID NO:6)

C-24         5'-CGGTAGCCGGCGGTATTGAGGGGGCTAGGTGGCTGT-3' (SEQ ID NO:7)

C-29         5'-CGGTAGCCGGCAGGTGGCTGTGGAGCCGGTACAATC-3' (SEQ ID NO:8)

C-34         5'-CGGTAGCCGGCCGGTACAATCTCTATTGGTGAGGAA-3' (SEQ ID NO:9)

C-39         5'-CGGTAGCCGGCTGGTGAGGAAGGGAGTCTTTGGTCG-3' (SEQ ID NO:10)
```

N-14 was also generated by PCR amplification of the corresponding region of the amphotropic hypervariable polyproline region:

Sense primer:

5'-GGTCCTAGGACCCCTCCCTTCCTCACCAATAGAGATTGTACCG-3' (SEQ ID NO:11)

Antisense primer:

5'-CGGTAGCCGGCTGGGGGTGGCTGTGGGACACTTGGAC-3' (SEQ ID NO:12)

The PCR conditions were as follows: 94° C., 1 min.; 55° C., 1 min; 72° C., 1 min; 25 cycles with a final extension at 72° C. for 5 minutes. The PCR primers were designed such that two restriction sites, AvrII and NgoMI, that also overhang the ecotropic hypervariable polyproline, were incorporated into the ends of the PCR products. The PCR products then were cleaved by AvrII and NgoMI, and cloned in between the AvrII and NgoMI sites created to flank the ecotropic hypervariable polyproline region to form the above-mentioned envelope expression plasmids.

The envelope expression plasmids C-44, C-49, C-54 were created by annealing sense and antisense oligonucleotides to generate double strand DNA fragments that were flanked by the sticky ends of AvrII and NgoMI. The DNA fragment then was cloned directly in between the AvrII and NgoMI sites of the modified CEE+ plasmid The oligonucleotides used are displayed below:

C-44

5'-CTAGGACCCCGAGTCCCCATAGGGCCCAACCCAGTATTACCCGACCAAAGA-3'  (SEQ ID NO:13)

3'-CTGGGGCTCAGGGGTATCCCGGGTTGGGTCATAATGGGCTGGTTTCTCGGCC-5'  (SEQ ID NO:14)

C-49

5'-CTAGGACCCCGAGTCCCCATAGGGCCCAACCCAGTAG-3'  (SEQ ID NO:15)

3'-CTGGGGCTCAGGGGTATCCCGGGTTGGGTCATCGGCC-5'  (SEQ ID NO:16)

C-54

5'-CTAGGACCCCGAGTCCCCATAG-3'  (SEQ ID NO:17)

3'CTGGGGCTCAGGGGTATCGGCC-5'  (SEQ ID NO:18)

Viral particles then were constructed by employing the transient three plasmid co-transfection system (Soneoka, et al., *Nucleic Acids Research*, Vol. 23, pgs. 628–633 (1995)) except that the modified envelope plasmids 5'-3', C-14, C-19, C-24, C-29, C-34, C-39, C-44, C-49, C-54, and N-14 were employed. Plasmid CEE+ also was employed in this example as a control. In this three plasmid co-transfection system, 10 μg each of (i) pHIT60; (ii) pHIT110 or pHIT112; and (iii) CEE+ or 5'-3', C-14, C-19, C-24, C-29, C-34, C-39, C-44, C-49, C-54, and N-14 were delivered by transient transfection of 70% confluent 293T cells expressing SV40 T-antigen in 10 cm culture dishes using calcium phosphate for 14–18 hours at 37° C., 5% $CO_2$. Plasmid pHIT60, provided by Dr. Paula Cannon, University of Oxford, Oxford, United Kingdom, includes the SV40 origin of replication and the retroviral gag-pol gene under the control of a cytomegalovirus (CMV) promoter. Plasmid pHIT110, also provided by Dr. Paula Cannon, includes a B-galactosidase (LacZ) gene under the control of a CMV promoter. Plasmid pHIT112, provided by Ling Li, USC Gene Therapy Laboratories, Los Angeles, Calif., includes a LacZ gene under the control of a hybrid CMV-LTR promoter, and a neomycin resistance gene under the control of the SV40 promoter. Plasmids pHIT60, pHIT110, and pHIT112 are described further in Soneoka, et al. (1995). The cultures then were treated with 6 ml of 10 mM sodium butyrate for 10 to 12 hours to optimize viral production. (Soneoka, et al. 1995.) The medium then was replaced with D10 and cultures were maintained at 37° C. for another 12 hours before harvesting the viral supernatants. The resulting viruses are referred to as CEE+ wild type, 5'-3', C-14, C-19, C-24, C-29, C-34, C-39, C-44, C-49, C-54, and N-14.

Viral titers (in cfu/ml) were determined by G418 resistant colony formation. $3 \times 10^4$ NIH 3T3 cells per 30 mm well were plated in 3 ml of DMEM containing 10% fetal calf serum (FCS). Such medium is known as D10. Eighteen to twenty-four hours later, the medium was replaced by 1 ml of serially diluted viral supernatant in the presence of Polybrene (8 μg/ml). After two hours of incubation at 37° C., an additional 2 ml of D10 was added. At about 18 to 24 hours post-transduction, the cells were selected for neomycin resistance with D10 containing G418 (0.6 mg/ml) for 10 days. Neomycin resistant colonies were scored by methylene blue staining.

For the chimeric envelope 5'-3', the virus titer was $1.7 \times 10^6$, comparable to the titer ($4.0 \times 10^6$) of virus bearing wild-type ecotropic envelope protein. This result indicates that the longer hypervariable polyproline did not seem to disrupt envelope function. The virus pseudotyped with C-14 achieved a titer of $3.5 \times 10^6$, suggesting that the length of the hypervariable polyproline region closest to the original size might serve the envelope function best; however, the N-14 mutant displayed a totally different phenotype. Although it carried the same length of hypervariable polyproline as the C-14 mutant, the virus titer was zero, which demonstrated that the N-terminal conserved 14 amino acids are essential for envelope function.

To test whether a longer hypervariable polyproline region would affect surface/transmembrane stability, a Western Blot was carried out to detect virion-associated envelope protein. It has been demonstrated that a weak surface protein/transmembrane protein interaction could be detected by freezing and thawing the virus sample (Zhao and Anderson, unpublished data). During this process, a large amount surface protein can be shed into the medium if there is a weak interaction between the surface protein and the transmembrane protein, resulting in a lower ratio of surface protein to transmembrane protein associated with the virion particle compared with the wild-type envelope protein. 5'-3', like CEE+ and C-14, displayed a wild-type level of envelope protein and a surface protein/transmembrane protein ratio associated with the viral particle (FIG. 3B), indicating that the additional length of hypervariable polyproline (at least up to 14 amino acids) did not seem to weaken the surface protein/transmembrane protein interaction.

To map the minimal length of hypervariable polyproline required for envelope protein function, serial truncations were made as hereinabove described, extending from the C-terminal toward the N-terminal end of the inserted amphotropic hypervariable polyproline (FIG. 2). Deletion of 34 amino acids, C-34, still achieved a virus titer of about $1.0 \times 10^6$, indicating that the envelope was almost as functional as the wild-type ecotropic envelope protein. When the deletion reached 39 amino acids from the C-terminal end of the inserted amphotropic hypervariable polyproline (C-39), the virus titer dropped ten-fold to $1.1 \times 10^5$. Even a deletion of 49 amino acids from the C-terminal end (C-49) reached a titer of $2.0 \times 10^5$. This result suggests that the envelope protein remained functional even though the majority of the hypervariable polyproline region was deleted. There was a sudden decrease of virus titer to 0 when the deletion entered 8 amino acids into the N-terminal conserved region (C-54). These results demonstrate that the hypervariable polyproline region, except for the conserved N-terminus, is flexible in terms of length and sequence. Truncation of most of the hypervariable polyproline region does not interfere drastically with envelope function; however, the N-terminal conserved region is essential for viral infectivity.

EXAMPLE 2

Figure 4A:
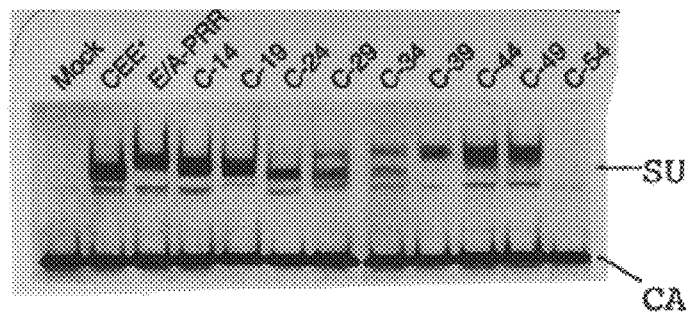
FIG. 4 shows the results of a Western Blot analysis to detect virion-associated envelope proteins of envelope mutants having serial truncations from the C-terminal end of the amphotropic hypervariable polyproline.
Figure 4B:

Detection of the serial deletion envelope mutants associated with the viral particle Western Blot analysis was carried out to examine the level of the serial deletion envelope mutants with the viral particle (FIG. 4). C-14 and C-19 contained envelope proteins in the viral particle at a level comparable to the wild type CEE+ and 5'-3'. This is correlated with the observation that the titers of viruses pseudotyped with C-14 and C-19 were similar to that of wild type CEE+. The envelope proteins associated with C-24, C-29 and C-34 gradually decreased as deletion went from 24 to 34 amino acids toward the N-terminal end of the hypervariable polyproline, as evidenced by the decreased level of both surface and transmembrane subunits associated with the viral particle. This indicates that a shortened hypervariable polyproline could cause a lower level of envelope proteins to be incorporated into the viral particle. Accordingly, there was a noticeable drop of the virus titer with C-34. For the surface protein of C-24, C-29 and C-34, in addition to a band detected at gp70 (surface) position, a band migrating at a higher position was also observed, and the intensity of the band increased as more amino acids were deleted. It is possible this band could be an isoform of gp70 or even uncleaved pr85 with an altered glycosylation pattern that caused the different migration on the gel. Further deletions from 39 to 49 amino acids toward the N-terminal conserved hypervariable polyproline region (C-39, C-44 and C-49) result in a diminishing level of surface protein at the gp70 position and a greatly decreased amount of transmembrane subunit associated with the viral particle. However, the intensity of the band migrating at the higher position increased to the extent that was comparable to the level of envelope protein in the wild type CEE+. This is not correlated to the lower viral titers of C-39, C-44 and C-49. One explanation is that the surface protein of such an abnormal migration has changed its antigenicity, possibly due to an altered glycosylation pattern. Thereby it interacts better with the antibody used in the Western Blot. This could account for the unexpectedly high surface/ transmembrane ratio observed for C-39, C-44 and C-49. C-54, which resulted from the deletion into the N-terminal conserved region, did not contain any detectable surface and transmembrane proteins in the virion particle. This result reflects the zero virus titer observed for C-54 in the transduction assay (FIG. 2).

In summary, there was a general tendency toward a decreased level of envelope protein incorporation when the hypervariable polyproline region was shortened. This correlates with lower virus titer when the hypervariable polyproline region was deleted.

EXAMPLE 3

Fusogenicity of the N-14 mutant

Figure 5A:
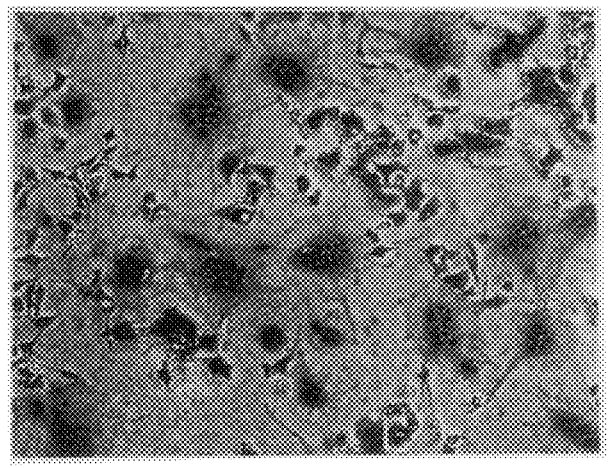
FIG. 5 shows the results of a fusion assay of the N-14 mutant. The fusion assay was carried out by cocultivation of 293T cells expressing the envelope protein and XC indicator cells containing the ecotropic receptor on the cell surface. The multinuclei cells in the figure, displaying the syncytia formed between 293T cells and XC indicator cells, demonstrate that N-14 and CEE+ produce a similar level of cell-to-cell fusion.
Figure 5B:
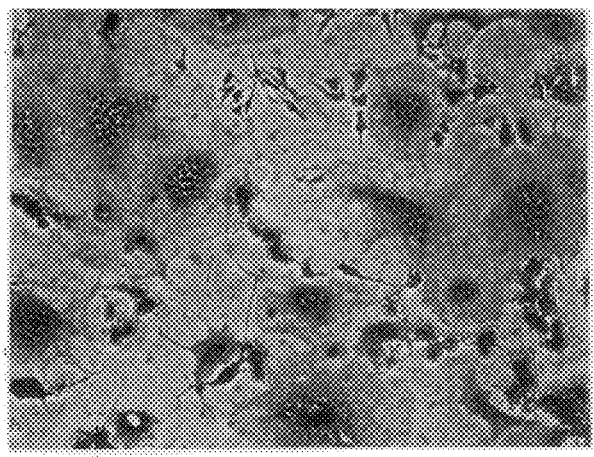
Figure 6A:
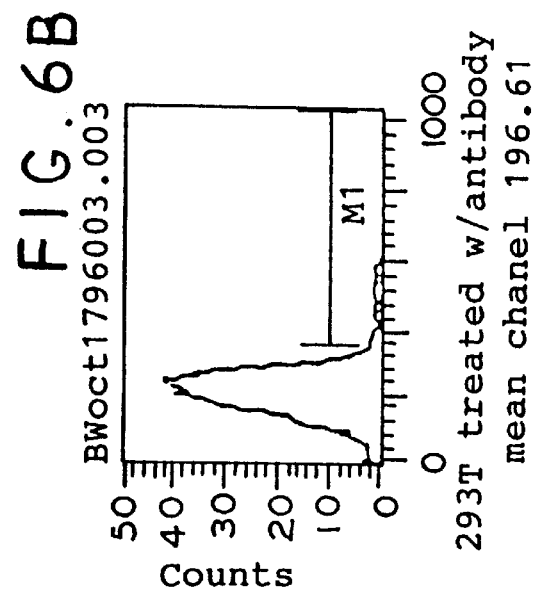
FIG. 6 shows the results of a FACS assay to examine the cell surface expression of the envelope protein. The figure shows the cell surface expression of envelope proteins CEE+ and N-14. The level of cell surface expression is judged by the mean channel shift comparing the 293T cell transfected with envelope proteins and the nontransfected cells. As shown in the figure, CEE+ and N-14 generate the same mean channel shift, indicating that both CEE+ and N-del have the similar cell surface expression.
Figure 6B:
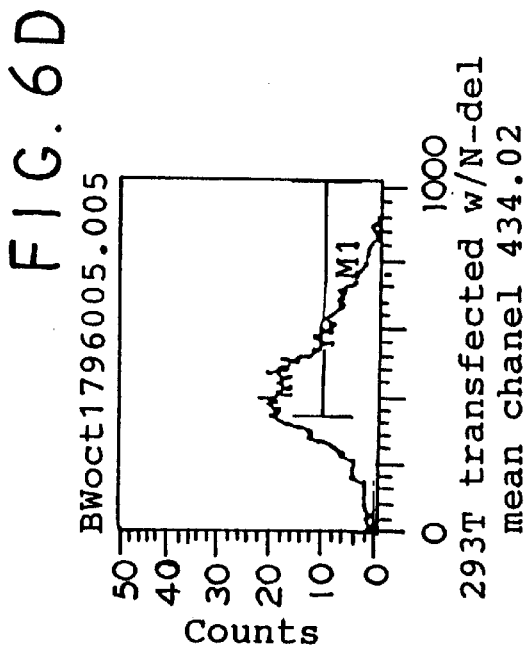
Figure 6C:
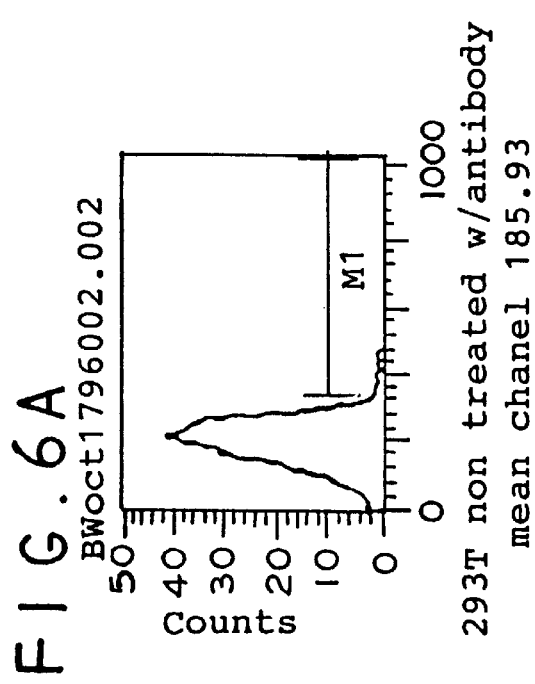
Figure 6D:
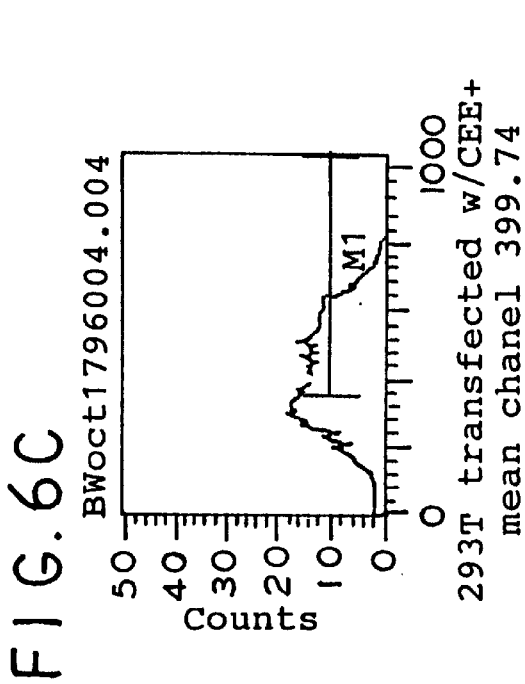

The hypervariable polyproline links region the N-terminal variable and the C-terminal conserved portions of the surface protein subunit. Because the N-terminal 14 amino acids of the hypervariable polyproline region are highly conserved between different species of murine leukemia viruses, it was considered that the N-terminal conserved region in the hypervariable polyproline region might be involved in the post-binding conformation change during viral entry. To test this hypothesis, a fusion assay was carried out to test the fusogenicity of the N-14 mutant. 293T cells expressing the envelope protein were cocultured with highly fusogenic XC indicator cells (ATCC No. CCL-165) that contained the ecotropic receptor. Binding of the envelope protein with its cognate receptor could trigger cell-cell fusion, generating syncytia. If the N-terminal conserved region were involved in post-binding events, the N-14 mutant would not trigger fusion even if it retained an intact receptor binding domain and could bind to the receptor on XC target cells. Unexpectedly, this fusion assay showed that the N-14 mutant was as fusogenic as the wild-type envelope protein (FIG. 5). This result suggested that the N-terminal conserved region may not participate directly in the post-binding conformation change.

EXAMPLE 4

Figure 3B:
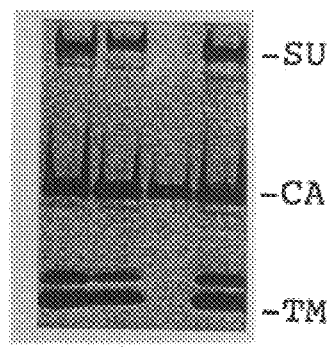
FIG. 3B Virion-associated envelope protein. The top band stands for surface protein. The middle band represents capsid protein. The bottom band shows the transmembrane protein.

Detection of N-14 envelope protein in producer cell lysate and in viral particles To determine whether the lack of infectivity of the N-14 mutant was caused by a defect in protein processing, Western Blot analysis was carried out to detect the envelope protein in producer cell lysates and in viral particles. The N-14 mutant, like the wild-type envelope protein (CEE+) and the C-14 mutant, was processed normally from the precursor to mature surface protein (FIG. 3A). FACS analysis was also conducted to examine the cell surface expression of the envelope protein (FIG. 6). The N-14 mutant had the same mean channel shift as the wild-type envelope protein, indicating that the envelope protein encoded by the N-14 mutant was transported normally to the producer cell surface. The virion-associated proteins also were analyzed by Western Blot (FIG. 3B). Both the wild-type envelope protein and the C-14 mutant had a similar level of surface protein and transmembrane protein associated with the viral particle; however, the N-14 mutant had little surface protein and transmembrane protein in the viral particle. Thus, the N-14 mutant is not infectious because there is no envelope protein on the surface of the virion to allow viral entry into the target cell.

There are at least two possibilities that could result in the lack of N-14 infectivity. Although the envelope protein was processed correctly and transported to the cell surface, it might not be incorporated into the viral particle during assembly. The other possibility is that there may be a significant shedding of surface protein from the viral particle after the envelope protein is incorporated into viral particles. Absence of surface protein could result in the unstable association of transmembrane protein with the virion (Kimberly, et al., *J. Virol.*, Vol. 67, pgs. 3489–3496 (1993)). This event could account for the failure to detect any transmembrane protein in viruses pseudotyped with N-14.

EXAMPLE 5

N-14 is a temperature-sensitive mutant and can be rescued by cotransfection with another envelope mutant There is no detectable N-14 envelope protein in the viral particle. The harvest of viruses at 32° C. was attempted, considering that envelope protein would be more stable at this temperature. When assembly of virions pseudotyped with N-14 was carried out at 32° C., the virus titer, determined as hereinabove described, increased from 0 to 1.4× $10^4$. As a comparison, the titer for CEE+ at 32° C. was 1.4×$10^5$. This result shows that N-14 is a temperature sensitive mutant.

Figure 7:
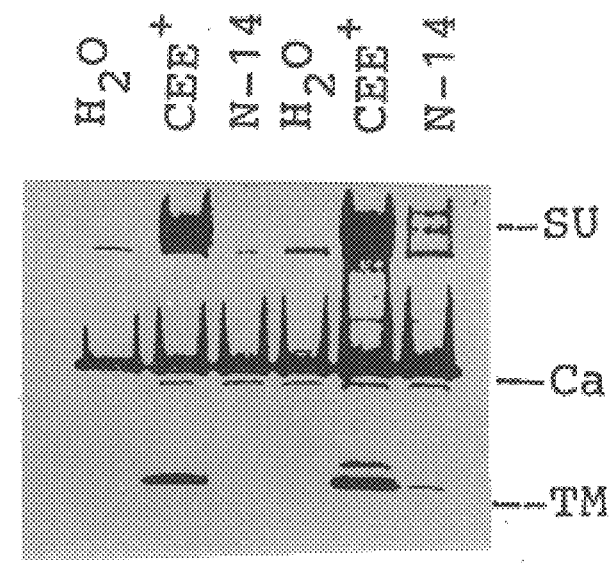
FIG. 7 is a Western Blot analysis showing that the N-14 mutant envelope was incorporated into the virion particle at 32° C. There was no detectable envelope protein associated with the N-14 mutant at 37° C.

Western Blot analysis showed that the N-14 mutant was incorporated into the virion particle at 32° C. (FIG. 7). Compared with wild type CEE+, the level of surface and transmembrane proteins in N-14 was much lower. Because the transmembrane domain was not detectable in N-14 at 37° C., it was considered that N-14 more likely is an incorporation mutant instead of a shedding mutant. In a shedding mutant, the interaction between the surface and transmembrane domains is disrupted such that the surface domain is separated from the transmembrane domain and sheds from the virus. For such a mutant, a reduced amount of surface domain or surface protein associated with the viral particle was observed; however, the transmembrane protein usually should still be present in the viral particle.

The N-14 also was cotransfected with the binding defective mutant D84K (MacKrell, et al., *J. Virol.*, Vol. 70, pgs. 1768–1774 (1996) that contained an intact hypervariable polyproline region including the N-terminal conserved region. Cotransfection resulted in a virus titer of 2.0×$10^5$ at 37° C., which indicates that the temperature-sensitive phenotype of the N-14 mutant could be rescued by the D84K mutant in trans. Because both the N-14 homo-oligomer and the D84K homo-oligomer cannot give titer on 3T3 cells, the rescue of the titer could be interpreted best as resulting from the coexistence of N-del and D84K in a hetero-oligomer.

EXAMPLE 6

Insertion of a collagen binding peptide into the hypervariable polyproline region Plasmid 5'-3' as described in Example 1, was modified by the addition of PstI and StuI cloning sites to form pEA (pst-stu). As a result of such modification, the codon encoding amino acid residue 35 of the polynucleotide encoding the amphotropic hypervariable polyproline region encodes glutamine (Gln) instead of asparagine (Asp), the codon encoding amino acid residue 48 of the polynucleotide encoding the amphotropic hypervariable polyproline region encodes glycine (Gly) instead of threonine (Thr), and the codon encoding amino acid residue 49 of the amphotropic hypervariable polyproline region encodes leucine (Leu) instead of serine (Ser).

Collagen binding domain sequences with linkers, hereinafter referred to Inserts 1 through 4, were inserted into pEA (pst-stu).

Insert 1 is a polynucleotide encoding the polypeptide GHMWREPSFMALSGAS (SEQ ID NO:19). The sequence was amplified using the following PCR primers:

Sense: 5'-CC TGA AGC ACC GCT CAG AGC CAT GAA GCT CGG TTC GCG CCA CAT ATG GCC CTG CA-3' (SEQ ID NO:20)

Antisense: 5'-G GGC CAT ATG TGG CGC GAA CCG AGC TTC ATG GCT CTG AGC GGT GCT TCA GG-3' (SEQ ID NO:21)

Insert 2 is a polynucleotide encoding the polypeptide GAMWREPSFMALSGAS (SEQ ID NO:22). The sequence was amplified using the following PCR primers:

Sense: 5'-G GGC GCT ATG TGG CGC GAA CCG AGC TTC ATG GCT CTG AGC GCT TCA GG-3' (SEQ ID NO:23)

Antisense: 5'-CC TGA AGC ACC GCT CAG AGC CAT GAA GCT CGG TTC GCG CCA CAT AGC GCC CTG CA-3' (SEQ ID NO:24)

Insert 3 is a polynucleotide encoding the same polypeptide as Insert 1. The sequence was amplified by using the following PCR primers:

Sense: 5'-G GGC CAT ATG TGG CGC GAA CCG AGC TTC ATG GCT CTG AGC GGT GCT AGC CTG CA-3' (SEQ ID NO:25)

Antisense: 5'-G GCT AGC ACC GCT CAG AGC CAT GAA GCT CGG TTC GCG CCA CAT ATG GCC CTG CA-3' (SEQ ID NO:26)

Insert 4 is a polynucleotide encoding the same polypeptide as Insert 2.

The sequence was amplified using the following PCR primers:

Sense: 5'-G GGC GCT ATG TGG CGC GAA CCG AGC TTC ATG GCT CTG AGC GGT GCT AGC CTG CA-3' (SEQ ID NO:27)

Antisense: 5'-G GCT AGC ACC GCT CAG AGC CAT GAA GCT CGG TTC GCG CCA CAT AGC GCC CTG CA-3' (SEQ ID NO:28)

PCR conditions for amplifying each of Inserts 1 through 4 were as follows: 94° C., 1 minute; 55° C., 10 seconds; 72° C., 10 seconds; 35 cycles with a final extension at 72° C. for 5 minutes.

Plasmid pEA (pst-stu) was digested with PstI and StuI, and ligated to the annealed oligonucleotides containing Insert 1 or Insert 2. The presence of the proper insert was confirmed by DNA sequencing. In the resulting plasmids, the polynucleotide encoding amino acid residues 34 to 49 of the amphotropic hypervariable polyproline region has been replaced with a polynucleotide encoding GHMWREPSFMALSGAS or GAMWREPSFMALSGAS. The resulting plasmids are known as pEA (Insert 1) and pEA (Insert 2), respectively.

Plasmid pEA also was digested with PstI, and ligated to Insert 3 or Insert 4. The presence of the proper insert was confirmed by DNA sequencing. In the resulting plasmids, known as pEA (Insert 3) and pEA (Insert 4), respectively, a polynucleotide encoding GHMWREPSFMALSGAS or GAMWREPSFMALSGAS is inserted between codon 35 and codon 36 of the amphotropic hypervariable polyproline region.

Viral particles then were constructed by employing the transient three plasmid co-transfection system (Soneoka, et al., *Nucleic Acids Research*, Vol. 23, pgs. 628–633 (1995)) except that the modified envelope plasmids pEA, pEA (Insert 1), pEA (Insert 2), pEA (Insert 3), or pEA (Insert 4) were employed. Plasmid CEE+ also was employed in this example as a control. In this three plasmid co-transfection system, 10 μg each of (i) pHIT60; (ii) pHIT110 or pHIT112; and (iii) CEE+ or pEA, pEA (Insert 1), pEA (Insert 2), pEA (Insert 3), or pEA (Insert 4) were delivered by transient transfection of 70% confluent 293T cells expressing SV40 T-antigen in 10 cm culture dishes using calcium phosphate for 14–18 hours at 37° C., 5% $CO_2$. Plasmid pHIT60, provided by Dr. Paula Cannon, University of Oxford, Oxford, United Kingdom, includes the SV40 origin of replication and the retroviral gag-pol gene under the control of a cytomegalovirus (CMV) promoter. Plasmid pHIT110, also provided by Dr. Paula Cannon, includes a B-galactosidase (LacZ) gene under the control of a CMV promoter. Plasmid pHIT112, provided by Ling Li, USC Gene Therapy Laboratories, Los Angeles, Calif., includes a LacZ gene under the control of a hybrid CMV-LTR promoter, and a neomycin resistance gene under the control of the SV40 promoter. Plasmids pHIT60, pHIT110, and pHIT112 are described further in Soneoka, et al. (1995). The cultures then were treated with 6 ml of 10 mM sodium butyrate for 10 to 12 hours to optimize viral production. (Soneoka, et al. 1995.) The medium then was replaced with D10 and cultures were maintained at 37° C. for another 12 hours before harvesting the viral supernatants. The resulting viruses are referred to as CEE wild type, CEE (CAE Hinge), Insert 1 virus, Insert 2 virus, Insert 3 virus, and Insert 4 virus.

Viral titers were determined based on expression of the neomycin resistance and/or the β-galactosidase reporter genes. 2.5×10⁴ NIH 3T3 cells were plated in each of 6-well plates one day prior to transduction. The medium was replaced with 1 ml of serial dilutions of viral supernatant with 8 µg/ml Polybrene for 2 hours, after which 1 ml of fresh D10 was added to the cultures, which then were maintained overnight at 37° C., 5% $CO_2$, after which G418 (800 µg/ml) was added and G418 resistant colonies were counted 10 days later and expressed as G418-resistant colony-forming units (cfu)/ml. For expression of β-galactosidase, the respective cultures were stained with X-gal 48 hours after transduction of NIH 3T3 cells. Viral titers for each virus are given in Table I below.

TABLE I

| Virus | Titer |
| --- | --- |
| CEE wild type | $3.8 \times 10^6 \pm 0.28 \times 10^6$ |
| CEE (CAE Hinge) | $2.3 \times 10^6 \pm 1.27 \times 10^6$ |
| Insert 1 virus | $1.4 \times 10^6 \pm 0.14 \times 10^6$ |
| Insert 2 virus | $1.5 \times 10^6 \pm 0.56 \times 10^6$ |
| Insert 3 virus | $1.6 \times 10^6 \pm 0.14 \times 10^6$ |
| Insert 4 virus | $1.1 \times 10^6 \pm 0.14 \times 10^6$ |

Figure 8:
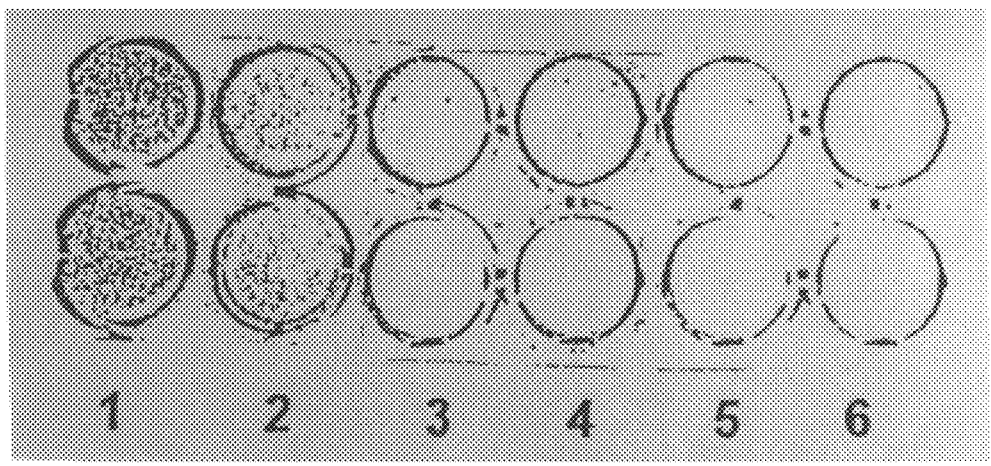
FIG. 8 shows results of an ELISA assay using collagen-coated wells for determining collagen binding by viruses having a modified envelope hypervariable polyproline region including a collagen bin including single-chain antibodies, monoclonal antibodies, and polyclonal antibodies. Such antibodies include, but are not limited to, antibodies and fragments or portions thereof which bind to erb-B2, such as, for example, e23 antibody; antibodies which bind to receptors such as, for example, the CD4 receptor on T-cells; antibodies which bind to the transferrin receptor; antibodies directed against human leukocyte antigen (HLA); antibodies to carcinoembryonic antigen; antibodies to placental alkaline phosphatase found on testicular and ovarian cancer cells; antibodies to high molecular weight melanoma-associated antigen; antibodies to polymorphic epithelial mucin found on ovarian cancer cells; antibodies to β-human chorionic gonadotropin; antibodies to CD20 antigen of B-lymphoma cells; antibodies to alphafetoprotein; antibodies to prostate specific antigen; OKT-3 antibody, which binds to CD3 T-lymphocyte surface antigen; antibodies which bind to B-lymphocyte surface antigen; antibodies which bind to EGFR (c-erb-B1 or c-erb-B2) found on glioma cells, B-cell lymphoma cells, and breast cancer cells; anti-tac monoclonal antibody, which binds to the Interleukin-2 receptor; anti-transferrin monoclonal antibodies; monoclonal antibodies to gp 95/gp 97 found on melanoma cells; monoclonal antibodies to p-glycoproteins; monoclonal antibodies to cluster-1 antigen (N-CAM), cluster-w4, cluster-5A, or cluster-6 (LeY), all found on small cell lung carcinomas; monoclonal antibodies to placental alkaline phosphatase; monoclonal antibodies to CA-125 found on lung and ovarian carcinoma cells, monoclonal antibodies to epithelial specific antigen (ESA) found on lung and ovarian carcinoma cells; monoclonal antibodies to CD19, CD22, and CD37 found on B-cell lymphoma cells; monoclonal antibodies to the 250 kDa proteoglycan found on melanoma cells; monoclonal antibodies to p55 protein found on breast cancer cells; monoclonal antibodies to the TCR-IgH fusion protein found on childhood T-cell leukemia cells; antibodies to T-cell antigen receptors; antibodies to tumor specific antigen on B-cell lymphomas; antibodies to organ cell surface markers; anti-HIV antibodies, such as anti-HIV gp 120-specific immunoglobulin, and anti-erythrocyte antibodies.

100 µl of viral supernatant, containing Insert 1 virus, Insert 2 virus, or CEE wild type virus, were placed on collagen-coated wells at room temperature for 30 minutes, washed twice with 1× PBS (sodium phosphate buffer, pH 7.4), and then tested for the presence of collagen-bound virions using a modified ELISA assay with a rat monoclonal antibody 83A25 (Evans, et al., *J. Virol.*, Vol. 64, No. 12, pgs. 6176–6183 (1990)), a secondary goat anti-rat IgG (1:50 dilution; Zymed, Inc.) that recognized the primary and tertiary antibody, and a tertiary rat peroxidase anti-peroxidase antibody (1:50 dilution, Sternberger-Mayer, Inc.) The primary antibody was incubated for 1 hour at room temperature and the secondary and tertiary antibodies were incubated for 30 minutes at room temperature. After treatment with each antibody, the wells were washed once with PBS. Immunoprecipates were identified microscopically after incubation with the chromogen diaminobenzidine. Such ELISA assay also is described further in Press, et al., *Cancer Research*, Vol. 53, pgs. 4960–4970 (1993). As shown in FIG. 8, lanes 1 and 2, containing collagen and Insert 1 virus and Insert 2 virus, respectively, were positive for collagen-bound virus, while lanes 3–6 were negative for collagen-bound virus. Lane 3 contained collagen and DMEM plus 10% FBS (blank control). Lane 4 contained collagen and CEE wild type virus, Lanes 5 and 6 did not contain collagen, but did contain Insert 1 virus and Insert 2 virus, respectively. We observed that Insert 1 virus bound to the collagen-coated plate more strongly than Insert 2 virus. Insert 1 virus contained a histidine residue in the collagen-binding domain. Histidine residue is usually exposed on the surface of protein. Existence of the histidine residue would therefore help the exposure of the collagen-binding domain to the surface of the envelope protein. This could account for the observed tighter binding of Insert 1 virus to the colage-coated plate From the above results, it is shown that virions pseudotyped with envelopes bearing a collagen-binding domain at the hypervariable polyproline region of gp70 were bound to collagen, while wild type CEE virions were washed away.

EXAMPLE 7

Transduction of NIH 3T3 cells by collagen-bound viruses pseudotyped by the chimeric envelopes In order to investigate whether the viruses pseudotyped with the chimeric envelope protein can transduce 3T3 cells after binding to the collagen, Insert 1 virus and Insert 3 virus were bound to collagen coated plates. After washing by PBS, the collagen coated wells were overlayed with NIH 3T3 cells. After 48 hours of incubation, the cells were stained by X-gal to determine the transduction. The results showed that the transduction efficiency for the viruses pseudotyped with the chimeric envelope was about 5% for Insert 1 virus and about 15% for Insert 3 virus. As a control, the viruses pseudotyped by wild type CEE+ could not transduce 3T3 cells because the viruses could not bind to the collagen coated plate.

The disclosures of all patents, publications (including published patent applications), database accession numbers, and depository accession numbers referenced in this specification are specifically incorporated herein by reference in their entirety to the same extent as if each such individual patent, publication, database accession number, and depository accession number were specifically and individually indicated to be incorporated by reference.

It is to be understood, however, that the scope of the present invention is not to be limited to the specific embodiments described above. The invention may be practiced other than as particularly described and still be within the scope of the accompanying claims.

What is claimed is:

1. A retroviral vector particle having a modified retroviral envelope polypeptide, said retroviral envelope polypeptide including the hypervariable polyproline region, wherein said hypervariable polyproline region is modified to include a targeting polypeptide including a binding region which binds to a ligand, and said retroviral vector particle including at least one polynucleotide encoding a therapeutic agent.

2. The retroviral vector particle of claim 1 wherein prior to modification the hypervariable polyproline region of said envelope has the sequence (SEQ ID NO:1), and in the modified polypeptide, amino acid residues 34 through 49 of (SEQ ID NO:1) are removed and replaced with the targeting polypeptide.

3. The retroviral vector particle of claim 1 wherein prior to modification the hypervariable polyproline region of said envelope has the sequence (SEQ ID NO:1), and in the modified polypeptide, amino acid residue 35 is changed from asparagine to glutamine, amino acid residue 48 is changed from threonine to glycine, and amino acid residue 49 is changed from serine to leucine, and the targeting polypeptide is inserted between amino acid residues 35 and 36 of (SEQ ID NO:1).

4. The retroviral vector particle of claim 1 wherein said ligand is an extracellular matrix component.

5. The retroviral vector particle of claim 4 wherein said extracellular matrix component is collagen.

6. The retroviral vector particle of claim 5 wherein said binding region which binds to collagen has the following structure: Trp-Arg-Glu-Pro-Ser-Phe-Met-Ala-Leu-Ser.

7. A modified polynucleotide encoding a modified retroviral envelope polypeptide, said retroviral envelope polypeptide including the hypervariable polyproline region, wherein, prior to modification, the polynucleotide encoding the hypervariable polyproline region encodes a hypervariable polyproline region having the sequence (SEQ ID NO:1), and in the modified polynucleotide, the codons encoding amino acid residues 34 through 49 of (SEQ ID NO:1) are removed and replaced with the polynucleotide encoding said targeting polypeptide.

8. A retroviral plasmid vector including the modified polynucleotide of claim 7.

9. A producer cell for producing a retroviral vector particle having a modified envelope polypeptide, said producer cell including the modified polynucleotide of claim 7.

10. A method of generating retroviral vector particles, comprising:

(a) transfecting a cell line selected from the group consisting of (i) a pre-packaging cell line including polynucleotides encoding the gag and pol retroviral proteins; and (ii) a packaging cell line including polynucleotides encoding the gag, pol, and env retroviral proteins with the retroviral plasmid vector of claim 8 to form a producer cell line; (b) culturing said producer cell line to generate retroviral vector particles; and (c) recovering said retroviral vector particles generated from said producer cell line.

11. A modified polynucleotide encoding a modified retroviral envelope polypeptide, said retroviral envelope polypeptide including the hypervariable polyproline region, wherein, prior to modification, the polynucleotide encoding the hypervariable polyproline region encodes a hypervariable polyproline region having the sequence (SEQ ID NO:1), and in the modified polynucleotide, the codon encoding amino acid residue 35 is changed such that the codon encoding amino acid residue 35 encodes glutamate, the codon encoding amino acid residue 48 is changed such that the codon encoding amino acid residue 48 encodes glycine, and the codon encoding amino acid residue 49 is changed such that the codon encoding amino acid residue 49 encodes leucine, and the polynucleotide encoding the targeting polypeptide is inserted between the codon encoding amino acid residue 35 and the codon encoding amino acid residue 36 of (SEQ ID NO: 1).

12. A retroviral plasmid vector including the modified polynucleotide of claim 11.

13. A producer cell for producing a retroviral vector particle having a modified envelope polypeptide, said producer cell including the modified polynucleotide of claim 11.

14. A method of generating retroviral vector particles, comprising:

(a) transfecting a cell line selected from the group consisting of (i) a pre-packaging cell line including polynucleotides encoding the gag and pol retroviral proteins; and (ii) a packaging cell line including polynucleotides encoding the gag, pol, and env retroviral proteins with the retroviral plasmid vector of claim 12 to form a producer cell line; (b) culturing said producer cell line to generate retroviral vector particles; and (c) recovering said retroviral vector particles generated from said producer cell line.

* * * * *

```
                    SEQUENCE LISTING (1) GENERAL INFORMATION:

(iii) NUMBER OF SEQUENCES:  41

(2) INFORMATION FOR SEQ ID NO: 1:

(i) SEQUENCE CHARACTERISTICS:
          (A) LENGTH:  60 amino acids
          (B) TYPE:  amino acid
          (C) STRANDEDNESS:
          (D) TOPOLOGY:  linear
```

(ii) MOLECULE TYPE: polypeptide (ix) FEATURE:
             (A) NAME/KEY:Hypervariable polyproline region of amphotropic
                 gp70 protein (xi) SEQUENCE DESCRIPTION: SEQ ID NO: 1:

Gly Pro Arg Val Pro Ile Gly Pro Asn Pro
 1               5                  10

Val Leu Pro Asp Gln Arg Leu Pro Ser Ser
                15                  20

Pro Ile Glu Ile Val Pro Ala Pro Gln Pro
                25                  30

Pro Ser Pro Leu Asn Thr Ser Tyr Pro Pro
                35                  40

Ser Thr Thr Ser Thr Pro Ser Thr Ser Pro
                45                  50

Thr Ser Pro Ser Val Pro Gln Pro Pro Pro
                55                  60

(2) INFORMATION FOR SEQ ID NO: 2:

(i) SEQUENCE CHARACTERISTICS:
            (A) LENGTH: 180 bases
            (B) TYPE: nucleic acid
            (C) STRANDEDNESS: single
            (D) TOPOLOGY: linear (ii) MOLECULE TYPE: polynucleotide (ix) FEATURE:
             (A) NAME/KEY:polynucleotide encoding hypervariable polyproline
                 region of amphotropic gp 70

(xi) SEQUENCE DESCRIPTION: SEQ ID NO: 2:

GGACCCCGAG TCCCCATAGG GCCCAACCCA GTATTACCCG ACCAAAGACT CCCTTCCTCA      60

CCAATAGAGA TTGTACCGGC TCCACAGCCA CCTAGCCCCC TCAATACCAG TTACCCCCCT     120

TCCACTACCA GTACACCCTC AACCTCCCCT ACAAGTCCAA GTGTCCCACA GCCACCCCCA     180

(2) INFORMATION FOR SEQ ID NO: 3:

(i) SEQUENCE CHARACTERISTICS:
            (A) LENGTH: 34 bases
            (B) TYPE: nucleic acid
            (C) STRANDEDNESS: single
            (D) TOPOLOGY: linear (ii) MOLECULE TYPE: polynucleotide (ix) FEATURE:
             (A) NAME/KEY:PCR primer (xi) SEQUENCE DESCRIPTION: SEQ ID NO: 3:

GACCTCCTAG GACCCCGAGT CCCCATAGGG CCCA                                  34

(2) INFORMATION FOR SEQ ID NO: 4:

(i) SEQUENCE CHARACTERISTICS:
            (A) LENGTH: 37 bases
            (B) TYPE: nucleic acid
            (C) STRANDEDNESS: single
            (D) TOPOLOGY: linear (ii) MOLECULE TYPE: polynucleotide (ix) FEATURE:

(A) NAME/KEY:PCR primer (xi) SEQUENCE DESCRIPTION: SEQ ID NO: 4:

CGGTAGCCGG CTGGGGGTGG CTGTGGGACA CTTGGAC                37

(2) INFORMATION FOR SEQ ID NO: 5:

(i) SEQUENCE CHARACTERISTICS:
            (A) LENGTH: 35 bases
            (B) TYPE: nucleic acid
            (C) STRANDEDNESS: single
            (D) TOPOLOGY: linear (ii) MOLECULE TYPE: polynucleotide (ix) FEATURE:
            (A) NAME/KEY:PCR primer (xi) SEQUENCE DESCRIPTION: SEQ ID NO: 5:

CGGTAGCCGG CGGGTGTACT GGTAGTGGAG GGGGG                  35

(2) INFORMATION FOR SEQ ID NO: 6:

(i) SEQUENCE CHARACTERISTICS:
            (A) LENGTH: 36 bases
            (B) TYPE: nucleic acid
            (C) STRANDEDNESS: single
            (D) TOPOLOGY: linear (ii) MOLECULE TYPE: polynucleotide (ix) FEATURE:
            (A) NAME/KEY:PCR primer (xi) SEQUENCE DESCRIPTION: SEQ ID NO: 6:

CGGTAGCCGG CGGAAGGGGG GTAACTGGTA TTGAGG                 36

(2) INFORMATION FOR SEQ ID NO: 7:

(i) SEQUENCE CHARACTERISTICS:
            (A) LENGTH: 36 bases
            (B) TYPE: nucleic acid
            (C) STRANDEDNESS: single
            (D) TOPOLOGY: linear (ii) MOLECULE TYPE: polynucleotide (ix) FEATURE:
            (A) NAME/KEY:PCR primer (xi) SEQUENCE DESCRIPTION: SEQ ID NO: 7:

CGGTAGCCGG CGGTATTGAG GGGGCTAGGT GGCTGT                 36

(2) INFORMATION FOR SEQ ID NO: 8:

(i) SEQUENCE CHARACTERISTICS:
            (A) LENGTH: 36 bases
            (B) TYPE: nucleic acid
            (C) STRANDEDNESS: single
            (D) TOPOLOGY: linear (ii) MOLECULE TYPE: polynucleotide (ix) FEATURE:
            (A) NAME/KEY:PCR primer (xi) SEQUENCE DESCRIPTION: SEQ ID NO: 8:

CGGTAGCCGG CAGGTGGCTG TGGAGCCGGT ACAATC                 36

(2) INFORMATION FOR SEQ ID NO: 9:

```
      (i) SEQUENCE CHARACTERISTICS:
          (A) LENGTH: 36 bases
          (B) TYPE: nucleic acid
          (C) STRANDEDNESS: single
          (D) TOPOLOGY: linear (ii) MOLECULE TYPE: polynucleotide (ix) FEATURE:
          (A) NAME/KEY:PCR primer (xi) SEQUENCE DESCRIPTION: SEQ ID NO: 9:

CGGTAGCCGG CCGGTACAAT CTCTATTGGT GAGGAA                                36

(2) INFORMATION FOR SEQ ID NO: 10:

(i) SEQUENCE CHARACTERISTICS:
          (A) LENGTH: 36 bases
          (B) TYPE: nucleic acid
          (C) STRANDEDNESS: single
          (D) TOPOLOGY: linear (ii) MOLECULE TYPE: polynucleotide (ix) FEATURE:
          (A) NAME/KEY:PCR primer (xi) SEQUENCE DESCRIPTION: SEQ ID NO: 10:

CGGTAGCCGG CTGGTGAGGA AGGGAGTCTT TGGTCG                                36

(2) INFORMATION FOR SEQ ID NO: 11:

(i) SEQUENCE CHARACTERISTICS:
          (A) LENGTH: 43 bases
          (B) TYPE: nucleic acid
          (C) STRANDEDNESS: single
          (D) TOPOLOGY: linear (ii) MOLECULE TYPE: polynucleotide (ix) FEATURE:
          (A) NAME/KEY:PCR primer (xi) SEQUENCE DESCRIPTION: SEQ ID NO: 11:

GGTCCTAGGA CCCCTCCCTT CCTCACCAAT AGAGATTGTA CCG                        43

(2) INFORMATION FOR SEQ ID NO: 12:

(i) SEQUENCE CHARACTERISTICS:
          (A) LENGTH: 37 bases
          (B) TYPE: nucleic acid
          (C) STRANDEDNESS: single
          (D) TOPOLOGY: linear (ii) MOLECULE TYPE: polynucleotide (ix) FEATURE:
          (A) NAME/KEY:PCR primer (xi) SEQUENCE DESCRIPTION: SEQ ID NO: 12:

CGGTAGCCGG CTGGGGGTGG CTGTGGGACA CTTGGAC                               37

(2) INFORMATION FOR SEQ ID NO: 13:

(i) SEQUENCE CHARACTERISTICS:
          (A) LENGTH: 51 bases
          (B) TYPE: nucleic acid
          (C) STRANDEDNESS: single
          (D) TOPOLOGY: linear (ii) MOLECULE TYPE: polynucleotide
```

```
    (ix) FEATURE:
          (A) NAME/KEY:PCR primer (xi) SEQUENCE DESCRIPTION: SEQ ID NO: 13:

CTAGGACCCC GAGTCCCCAT AGGGCCCAAC CCAGTATTAC CCGACCAAAG A        51

(2) INFORMATION FOR SEQ ID NO: 14:

(i) SEQUENCE CHARACTERISTICS:
          (A) LENGTH:  52 bases
          (B) TYPE:  nucleic acid
          (C) STRANDEDNESS:  single
          (D) TOPOLOGY:  linear (ii) MOLECULE TYPE:  polynucleotide (ix) FEATURE:
          (A) NAME/KEY:PCR primer (xi) SEQUENCE DESCRIPTION: SEQ ID NO: 14:

CTGGGGCTCA GGGGTATCCC GGGTTGGGTC ATAATGGGCT GGTTTCTCGG CC        52

(2) INFORMATION FOR SEQ ID NO: 15:

(i) SEQUENCE CHARACTERISTICS:
          (A) LENGTH:  37 bases
          (B) TYPE:  nucleic acid
          (C) STRANDEDNESS:  single
          (D) TOPOLOGY:  linear (ii) MOLECULE TYPE:  polynucleotide (ix) FEATURE:
          (A) NAME/KEY:PCR primer (xi) SEQUENCE DESCRIPTION: SEQ ID NO: 15:

CTAGGACCCC GAGTCCCCAT AGGGCCCAAC CCAGTAG                         37

(2) INFORMATION FOR SEQ ID NO: 16:

(i) SEQUENCE CHARACTERISTICS:
          (A) LENGTH:  37 bases
          (B) TYPE:  nucleic acid
          (C) STRANDEDNESS:  single
          (D) TOPOLOGY:  linear (ii) MOLECULE TYPE:  polynucleotide (ix) FEATURE:
          (A) NAME/KEY:PCR primer (xi) SEQUENCE DESCRIPTION: SEQ ID NO: 16:

CTGGGGCTCA GGGGTATCCC GGGTTGGGTC ATCGGCC                         37

(2) INFORMATION FOR SEQ ID NO: 17:

(i) SEQUENCE CHARACTERISTICS:
          (A) LENGTH:  22 bases
          (B) TYPE:  nucleic acid
          (C) STRANDEDNESS:  single
          (D) TOPOLOGY:  linear (ii) MOLECULE TYPE:  polynucleotide (ix) FEATURE:
          (A) NAME/KEY:PCR primer (xi) SEQUENCE DESCRIPTION: SEQ ID NO: 17:

CTAGGACCCC GAGTCCCCAT AG                                         22
```

(2) INFORMATION FOR SEQ ID NO: 18:

(i) SEQUENCE CHARACTERISTICS:
        (A) LENGTH: 22 bases
        (B) TYPE: nucleic acid
        (C) STRANDEDNESS: single
        (D) TOPOLOGY: linear (ii) MOLECULE TYPE: polynucleotide (ix) FEATURE:
        (A) NAME/KEY:PCR primer (xi) SEQUENCE DESCRIPTION: SEQ ID NO: 18:

```
CTGGGGCTCA GGGGTATCGG CC                                             22
```

(2) INFORMATION FOR SEQ ID NO: 19:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: polypeptide (xi) SEQUENCE DESCRIPTION: SEQ ID NO: 19:

```
Gly His Met Trp Arg Glu Pro Ser Phe Met
1               5                   10

Ala Leu Ser Gly Ala Ser
            15
```

(2) INFORMATION FOR SEQ ID NO: 20:

(i) SEQUENCE CHARACTERISTICS:
        (A) LENGTH: 55 bases
        (B) TYPE: nucleic acid
        (C) STRANDEDNESS: single
        (D) TOPOLOGY: linear (ii) MOLECULE TYPE: polynucleotide (ix) FEATURE:
        (A) NAME/KEY:PCR primer (xi) SEQUENCE DESCRIPTION: SEQ ID NO: 20:

```
CCTGAAGCAC CGCTCAGAGC CATGAAGCTC GGTTCGCGCC ACATATGGCC CTGCA         55
```

(2) INFORMATION FOR SEQ ID NO: 21:

(i) SEQUENCE CHARACTERISTICS:
        (A) LENGTH: 51 bases
        (B) TYPE: nucleic acid
        (C) STRANDEDNESS: single
        (D) TOPOLOGY: linear (ii) MOLECULE TYPE: polynucleotide (ix) FEATURE:
        (A) NAME/KEY:PCR primer (xi) SEQUENCE DESCRIPTION: SEQ ID NO: 21:

```
GGGCCATATG TGGCGCGAAC CGAGCTTCAT GGCTCTGAGC GGTGCTTCAG G             51
```

(2) INFORMATION FOR SEQ ID NO: 22:

(i) SEQUENCE CHARACTERISTICS:
        (A) LENGTH: 16 amino acids
        (B) TYPE: amino acid
        (C) STRANDEDNESS:

(D) TOPOLOGY:  linear (ii) MOLECULE TYPE:  polypeptide (xi) SEQUENCE DESCRIPTION:  SEQ ID NO: 22:

Gly Ala Met Trp Arg Glu Pro Ser Phe Met
 1               5                  10

Ala Leu Ser Gly Ala Ser
             15

(2) INFORMATION FOR SEQ ID NO: 23:

(i) SEQUENCE CHARACTERISTICS:
            (A) LENGTH:  48 bases
            (B) TYPE:  nucleic acid
            (C) STRANDEDNESS:  single
            (D) TOPOLOGY:  linear (ii) MOLECULE TYPE:  polynucleotide (ix) FEATURE:
            (A) NAME/KEY:PCR primer (xi) SEQUENCE DESCRIPTION:  SEQ ID NO: 23:

GGGCGCTATG TGGCGCGAAC CGAGCTTCAT GGCTCTGAGC GCTTCAGG                48

(2) INFORMATION FOR SEQ ID NO: 24:

(i) SEQUENCE CHARACTERISTICS:
            (A) LENGTH:  55 bases
            (B) TYPE:  nucleic acid
            (C) STRANDEDNESS:  single
            (D) TOPOLOGY:  linear (ii) MOLECULE TYPE:  polynucleotide (ix) FEATURE:
            (A) NAME/KEY:PCR primer (xi) SEQUENCE DESCRIPTION:  SEQ ID NO: 24:

CCTGAAGCAC CGCTCAGAGC CATGAAGCTC GGTTCGCGCC ACATAGCGCC CTGCA          55

(2) INFORMATION FOR SEQ ID NO: 25:

(i) SEQUENCE CHARACTERISTICS:
            (A) LENGTH:  54 bases
            (B) TYPE:  nucleic acid
            (C) STRANDEDNESS:  single
            (D) TOPOLOGY:  linear (ii) MOLECULE TYPE:  polynucleotide (ix) FEATURE:
            (A) NAME/KEY:PCR primer (xi) SEQUENCE DESCRIPTION:  SEQ ID NO: 25:

GGGCCATATG TGGCGCGAAC CGAGCTTCAT GGCTCTGAGC GGTGCTAGCC TGCA           54

(2) INFORMATION FOR SEQ ID NO: 26:

(i) SEQUENCE CHARACTERISTICS:
            (A) LENGTH:  54 bases
            (B) TYPE:  nucleic acid
            (C) STRANDEDNESS:  single
            (D) TOPOLOGY:  linear (ii) MOLECULE TYPE:  polynucleotide (ix) FEATURE:
            (A) NAME/KEY:PCR primer

```
    (xi) SEQUENCE DESCRIPTION: SEQ ID NO: 26:

GGCTAGCACC GCTCAGAGCC ATGAAGCTCG GTTCGCGCCA CATATGGCCC TGCA          54

(2) INFORMATION FOR SEQ ID NO: 27:

(i) SEQUENCE CHARACTERISTICS:
         (A) LENGTH:  54 bases
         (B) TYPE:  nucleic acid
         (C) STRANDEDNESS:  single
         (D) TOPOLOGY:  linear (ii) MOLECULE TYPE:  polynucleotide (ix) FEATURE:
         (A) NAME/KEY:PCR primer (xi) SEQUENCE DESCRIPTION: SEQ ID NO: 27:

GGGCGCTATG TGGCGCGAAC CGAGCTTCAT GGCTCTGAGC GGTGCTAGCC TGCA          54

(2) INFORMATION FOR SEQ ID NO: 28:

(i) SEQUENCE CHARACTERISTICS:
         (A) LENGTH:  54 bases
         (B) TYPE:  nucleic acid
         (C) STRANDEDNESS:  single
         (D) TOPOLOGY:  linear (ii) MOLECULE TYPE:  polynucleotide (ix) FEATURE:
         (A) NAME/KEY:PCR primer (xi) SEQUENCE DESCRIPTION: SEQ ID NO: 28:

GGCTAGCACC GCTCAGAGCC ATGAAGCTCG GTTCGCGCCA CATAGCGCCC TGCA          54

(2) INFORMATION FOR SEQ ID NO: 29:

(i) SEQUENCE CHARACTERISTICS:
         (A) LENGTH:  45 amino acids
         (B) TYPE:  amino acid
         (C) STRANDEDNESS:
         (D) TOPOLOGY:  linear (ii) MOLECULE TYPE:  polypeptide (ix) FEATURE:
         (A) NAME/KEY:Ecotropic hypervariable polyproline region of a
             retroviral envelope (xi) SEQUENCE DESCRIPTION: SEQ ID NO: 29:

Gly Pro Arg Val Pro Ile Gly Pro Asn Pro
1               5                   10

Val Leu Ala Asp Gln Gln Pro Leu Ser Lys
                15                  20

Pro Lys Pro Val Lys Ser Pro Ser Val Thr
                25                  30

Lys Pro Pro Ser Gly Thr Pro Leu Ser Pro
                35                  40

Thr Gln Leu Pro Pro
                45

(2) INFORMATION FOR SEQ ID NO: 30:

(i) SEQUENCE CHARACTERISTICS:
         (A) LENGTH:  46 amino acids
         (B) TYPE:  amino acid
         (C) STRANDEDNESS:
         (D) TOPOLOGY:  linear
```

(ii) MOLECULE TYPE: polypeptide (xi) SEQUENCE DESCRIPTION: SEQ ID NO: 30:

```
Gly Pro Arg Val Pro Ile Gly Pro Asn Pro
1               5                   10

Val Leu Pro Asp Gln Arg Leu Pro Ser Ser
                15                  20

Pro Ile Glu Ile Val Pro Ala Pro Gln Pro
                25                  30

Pro Ser Pro Leu Asn Thr Ser Tyr Pro Pro
                35                  40

Ser Thr Thr Ser Thr Pro
                45
```

(2) INFORMATION FOR SEQ ID NO: 31:

(i) SEQUENCE CHARACTERISTICS:
        (A) LENGTH: 41 amino acids
        (B) TYPE: amino acid
        (C) STRANDEDNESS:
        (D) TOPOLOGY: linear (ii) MOLECULE TYPE: polypeptide (xi) SEQUENCE DESCRIPTION: SEQ ID NO: 31:

```
Gly Pro Arg Val Pro Ile Gly Pro Asn Pro
1               5                   10

Val Leu Pro Asp Gln Arg Leu Pro Ser Ser
                15                  20

Pro Ile Glu Ile Val Pro Ala Pro Gln Pro
                25                  30

Pro Ser Pro Leu Asn Thr Ser Tyr Pro Pro
                35                  40

Ser
```

(2) INFORMATION FOR SEQ ID NO: 32:

(i) SEQUENCE CHARACTERISTICS:
        (A) LENGTH: 36 amino acids
        (B) TYPE: amino acid
        (C) STRANDEDNESS:
        (D) TOPOLOGY: linear (ii) MOLECULE TYPE: polypeptide (xi) SEQUENCE DESCRIPTION: SEQ ID NO: 32:

```
Gly Pro Arg Val Pro Ile Gly Pro Asn Pro
1               5                   10

Val Leu Pro Asp Gln Arg Leu Pro Ser Ser
                15                  20

Pro Ile Glu Ile Val Pro Ala Pro Gln Pro
                25                  30

Pro Ser Pro Leu Asn Thr
                35
```

(2) INFORMATION FOR SEQ ID NO: 33:

(i) SEQUENCE CHARACTERISTICS:
        (A) LENGTH: 31 amino acids
        (B) TYPE: amino acid
        (C) STRANDEDNESS:
        (D) TOPOLOGY: linear (ii) MOLECULE TYPE:  polypeptide (xi) SEQUENCE DESCRIPTION:  SEQ ID NO: 33:

Gly Pro Arg Val Pro Ile Gly Pro Asn Pro
1               5                   10

Val Leu Pro Asp Gln Arg Leu Pro Ser Ser
                15                  20

Pro Ile Glu Ile Val Pro Ala Pro Gln Pro
                25                  30

Pro (2) INFORMATION FOR SEQ ID NO: 34:

(i) SEQUENCE CHARACTERISTICS:
        (A) LENGTH:  26 amino acids
        (B) TYPE:  amino acid
        (C) STRANDEDNESS:
        (D) TOPOLOGY:  linear (ii) MOLECULE TYPE:  polypeptide (xi) SEQUENCE DESCRIPTION:  SEQ ID NO: 34:

Gly Pro Arg Val Pro Ile Gly Pro Asn Pro
1               5                   10

Val Leu Pro Asp Gln Arg Leu Pro Ser Ser
                15                  20

Pro Ile Glu Ile Val Pro
                25

(2) INFORMATION FOR SEQ ID NO: 35:

(i) SEQUENCE CHARACTERISTICS:
        (A) LENGTH:  21 amino acids
        (B) TYPE:  amino acid
        (C) STRANDEDNESS:
        (D) TOPOLOGY:  linear (ii) MOLECULE TYPE:  polypeptide (xi) SEQUENCE DESCRIPTION:  SEQ ID NO: 35:

Gly Pro Arg Val Pro Ile Gly Pro Asn Pro
1               5                   10

Val Leu Pro Asp Gln Arg Leu Pro Ser Ser
                15                  20

Pro (2) INFORMATION FOR SEQ ID NO: 36:

(i) SEQUENCE CHARACTERISTICS:
        (A) LENGTH:  16 amino acids
        (B) TYPE:  amino acid
        (C) STRANDEDNESS:
        (D) TOPOLOGY:  linear (ii) MOLECULE TYPE:  polypeptide (xi) SEQUENCE DESCRIPTION:  SEQ ID NO: 36:

Gly Pro Arg Val Pro Ile Gly Pro Asn Pro
 1              5                   10

Val Leu Pro Asp Gln Arg
                15

(2) INFORMATION FOR SEQ ID NO: 37:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: polypeptide (xi) SEQUENCE DESCRIPTION: SEQ ID NO: 37:

```
Gly Pro Arg Val Pro Ile Gly Pro Asn Pro
 1               5                  10
Val
```

(2) INFORMATION FOR SEQ ID NO: 38:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: polypeptide (xi) SEQUENCE DESCRIPTION: SEQ ID NO: 38:

```
Gly Pro Arg Val Pro Ile
 1               5
```

(2) INFORMATION FOR SEQ ID NO: 39:

(i) SEQUENCE CHARACTERISTICS:
        (A) LENGTH: 46 amino acids
        (B) TYPE: amino acid
        (C) STRANDEDNESS:
        (D) TOPOLOGY: linear (ii) MOLECULE TYPE: polypeptide (xi) SEQUENCE DESCRIPTION: SEQ ID NO: 39:

```
Gln Arg Leu Pro Ser Ser Pro Ile Glu Ile
 1               5                  10
Val Pro Ala Pro Gln Pro Pro Ser Pro Leu
                15                  20
Asn Thr Ser Tyr Pro Pro Ser Thr Thr Ser
                25                  30
Thr Pro Ser Thr Ser Pro Thr Ser Pro Ser
                35                  40
Val Pro Gln Pro Pro Pro
                45
```

(2) INFORMATION FOR SEQ ID NO: 40:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: polypeptide (xi) SEQUENCE DESCRIPTION: SEQ ID NO: 40:

```
Cys Gln Ala Gly Thr Phe Ala Leu Arg Gly
                 5                  10
Asp Asn Pro Gln Gly Cys
                15
```

```
-continued (2) INFORMATION FOR SEQ ID NO: 41:

(i) SEQUENCE CHARACTERISTICS:
        (A) LENGTH:   15 amino acids
        (B) TYPE:   amino acid
        (C) STRANDEDNESS:
        (D) TOPOLOGY:   linear (ii) MOLECULE TYPE:   polypeptide (xi) SEQUENCE DESCRIPTION:   SEQ ID NO: 41:

Gly Glu Arg Gly Asp Gly Ser Phe Phe Ala
             5                   10

Phe Arg Ser Pro Phe
             15
```